United States Patent
Koop et al.

(10) Patent No.: US 10,874,861 B2
(45) Date of Patent: Dec. 29, 2020

(54) DUAL CHAMBER PACING WITHOUT BEAT-TO-BEAT COMMUNICATION

(71) Applicant: CARDIAC PACEMAKERS, INC., St. Paul, MN (US)

(72) Inventors: Brendan Early Koop, Ham Lake, MN (US); Jeffrey E. Stahmann, Ramsey, MN (US); Allan Charles Shuros, St. Paul, MN (US); Keith R. Maile, New Brighton, MN (US); Benjamin J. Haasl, Forest Lake, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 146 days.

(21) Appl. No.: 16/239,076

(22) Filed: Jan. 3, 2019

(65) Prior Publication Data

US 2019/0201696 A1    Jul. 4, 2019

Related U.S. Application Data

(60) Provisional application No. 62/613,598, filed on Jan. 4, 2018.

(51) Int. Cl.
*A61N 1/375*    (2006.01)
*A61N 1/365*    (2006.01)
(Continued)

(52) U.S. Cl.
CPC .......... *A61N 1/36585* (2013.01); *A61B 5/046* (2013.01); *A61N 1/3622* (2013.01);
(Continued)

(58) Field of Classification Search
CPC ................ A61N 1/3622; A61N 1/3627; A61N 1/36507; A61N 1/36564; A61N 1/36578;
(Continued)

(56) References Cited

U.S. PATENT DOCUMENTS

| 3,835,864 A | 9/1974 | Rasor et al. |
| 3,943,936 A | 3/1976 | Rasor et al. |

(Continued)

FOREIGN PATENT DOCUMENTS

| AU | 2008279789 B2 | 10/2011 |
| AU | 2008329620 B2 | 5/2014 |

(Continued)

OTHER PUBLICATIONS

US 8,886,318 B2, 11/2014, Jacobson et al. (withdrawn)
(Continued)

*Primary Examiner* — George Manuel
(74) *Attorney, Agent, or Firm* — Seager, Tufte & Wickhem LLP.

(57) ABSTRACT

A ventricular implantable medical device that is configured to detect an atrial timing fiducial from the ventricle. The ventricular implantable medical is configured to deliver a ventricular pacing therapy to the ventricle based on the detected atrial timing fiducial. If the ventricular implantable medical device temporarily fails to detect atrial activity because of noise, posture, patient activity or for any other reason, an atrial implantable medical device may be configured to communicate atrial events to the ventricular implantable medical device and the ventricular implantable medical device may synchronize the ventricular pacing therapy with the atrium activity based on those communications.

17 Claims, 6 Drawing Sheets

(51) Int. Cl.
*A61N 1/362* (2006.01)
*A61N 1/372* (2006.01)
*A61B 5/046* (2006.01)
*A61N 1/39* (2006.01)
*A61N 1/37* (2006.01)

(52) U.S. Cl.
CPC ....... *A61N 1/3627* (2013.01); *A61N 1/36507* (2013.01); *A61N 1/36564* (2013.01); *A61N 1/36578* (2013.01); *A61N 1/3706* (2013.01); *A61N 1/3756* (2013.01); *A61N 1/37223* (2013.01); *A61N 1/37288* (2013.01); *A61N 1/37512* (2017.08); *A61N 1/39622* (2017.08); *A61N 1/3702* (2013.01); *A61N 1/3758* (2013.01)

(58) Field of Classification Search
CPC .............. A61N 1/36585; A61N 1/3702; A61N 1/3706; A61N 1/37223; A61N 1/37288; A61N 1/37512; A61N 1/3756; A61N 1/3758; A61N 1/39622; A61B 5/046; A61B 8/12
See application file for complete search history.

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | DePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Rostami et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |

(56) References Cited

U.S. PATENT DOCUMENTS

| | | |
|---|---|---|
| 5,919,214 A | 7/1999 | Ciciarelli et al. |
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | DePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |

(56) References Cited

U.S. PATENT DOCUMENTS

| | | |
|---|---|---|
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |

(56) References Cited

U.S. PATENT DOCUMENTS

| | | |
|---|---|---|
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |

(56) References Cited

U.S. PATENT DOCUMENTS

| | | | |
|---|---|---|---|
| 8,788,053 | B2 | 7/2014 | Jacobson |
| 8,798,740 | B2 | 8/2014 | Samade et al. |
| 8,798,745 | B2 | 8/2014 | Jacobson |
| 8,798,762 | B2 | 8/2014 | Fain et al. |
| 8,798,770 | B2 | 8/2014 | Reddy |
| 8,805,505 | B1 | 8/2014 | Roberts |
| 8,805,528 | B2 | 8/2014 | Corndorf |
| 8,812,109 | B2 | 8/2014 | Blomqvist et al. |
| 8,818,504 | B2 | 8/2014 | Bodner et al. |
| 8,827,913 | B2 | 9/2014 | Havel et al. |
| 8,831,747 | B1 | 9/2014 | Min et al. |
| 8,855,789 | B2 | 10/2014 | Jacobson |
| 8,868,186 | B2 | 10/2014 | Kroll |
| 8,886,339 | B2 | 11/2014 | Faltys et al. |
| 8,903,473 | B2 | 12/2014 | Rogers et al. |
| 8,903,500 | B2 | 12/2014 | Smith et al. |
| 8,903,513 | B2 | 12/2014 | Ollivier |
| 8,909,336 | B2 | 12/2014 | Navarro-Paredes et al. |
| 8,914,131 | B2 | 12/2014 | Bornzin et al. |
| 8,923,795 | B2 | 12/2014 | Makdissi et al. |
| 8,923,963 | B2 | 12/2014 | Bonner et al. |
| 8,938,300 | B2 | 1/2015 | Rosero |
| 8,942,806 | B2 | 1/2015 | Sheldon et al. |
| 8,958,892 | B2 | 2/2015 | Khairkhahan et al. |
| 8,977,358 | B2 | 3/2015 | Ewert et al. |
| 8,989,873 | B2 | 3/2015 | Locsin |
| 8,996,109 | B2 | 3/2015 | Karst et al. |
| 9,002,467 | B2 | 4/2015 | Smith et al. |
| 9,008,776 | B2 | 4/2015 | Cowan et al. |
| 9,008,777 | B2 | 4/2015 | Dianaty et al. |
| 9,014,818 | B2 | 4/2015 | Deterre et al. |
| 9,017,341 | B2 | 4/2015 | Bornzin et al. |
| 9,020,611 | B2 | 4/2015 | Khairkhahan et al. |
| 9,037,262 | B2 | 5/2015 | Regnier et al. |
| 9,042,984 | B2 | 5/2015 | Demmer et al. |
| 9,072,911 | B2 | 7/2015 | Hastings et al. |
| 9,072,913 | B2 | 7/2015 | Jacobson |
| 9,155,479 | B2 | 10/2015 | Solem |
| 9,155,882 | B2 | 10/2015 | Grubac et al. |
| 9,168,372 | B2 | 10/2015 | Fain |
| 9,168,380 | B1 | 10/2015 | Greenhut et al. |
| 9,168,383 | B2 | 10/2015 | Jacobson et al. |
| 9,180,285 | B2 | 11/2015 | Moore et al. |
| 9,192,774 | B2 | 11/2015 | Jacobson |
| 9,205,225 | B2 | 12/2015 | Khairkhahan et al. |
| 9,216,285 | B1 | 12/2015 | Boling et al. |
| 9,216,293 | B2 | 12/2015 | Berthiaume et al. |
| 9,216,298 | B2 | 12/2015 | Jacobson |
| 9,227,077 | B2 | 1/2016 | Jacobson |
| 9,238,145 | B2 | 1/2016 | Wenzel et al. |
| 9,242,102 | B2 | 1/2016 | Khairkhahan et al. |
| 9,242,113 | B2 | 1/2016 | Smith et al. |
| 9,248,300 | B2 | 2/2016 | Rys et al. |
| 9,265,436 | B2 | 2/2016 | Min et al. |
| 9,265,962 | B2 | 2/2016 | Dianaty et al. |
| 9,272,155 | B2 | 3/2016 | Ostroff |
| 9,278,218 | B2 | 3/2016 | Karst et al. |
| 9,278,229 | B1 | 3/2016 | Reinke et al. |
| 9,283,381 | B2 | 3/2016 | Grubac et al. |
| 9,283,382 | B2 | 3/2016 | Berthiaume et al. |
| 9,289,612 | B1 | 3/2016 | Sambelashvili et al. |
| 9,302,115 | B2 | 4/2016 | Molin et al. |
| 9,333,364 | B2 | 5/2016 | Echt et al. |
| 9,358,387 | B2 | 6/2016 | Suwito et al. |
| 9,358,400 | B2 | 6/2016 | Jacobson |
| 9,364,675 | B2 | 6/2016 | Deterre et al. |
| 9,370,663 | B2 | 6/2016 | Moulder |
| 9,375,580 | B2 | 6/2016 | Bonner et al. |
| 9,375,581 | B2 | 6/2016 | Baru et al. |
| 9,381,365 | B2 | 7/2016 | Kibler et al. |
| 9,393,424 | B2 | 7/2016 | Demmer et al. |
| 9,393,436 | B2 | 7/2016 | Doerr |
| 9,399,139 | B2 | 7/2016 | Demmer et al. |
| 9,399,140 | B2 | 7/2016 | Cho et al. |
| 9,409,033 | B2 | 8/2016 | Jacobson |
| 9,427,594 | B1 | 8/2016 | Bornzin et al. |
| 9,433,368 | B2 | 9/2016 | Stahmann et al. |
| 9,433,780 | B2 | 9/2016 | Régnier et al. |
| 9,457,193 | B2 | 10/2016 | Klimovitch et al. |
| 9,492,668 | B2 | 11/2016 | Sheldon et al. |
| 9,492,669 | B2 | 11/2016 | Demmer et al. |
| 9,492,674 | B2 | 11/2016 | Schmidt et al. |
| 9,492,677 | B2 | 11/2016 | Greenhut et al. |
| 9,511,233 | B2 | 12/2016 | Sambelashvili |
| 9,511,236 | B2 | 12/2016 | Varady et al. |
| 9,511,237 | B2 | 12/2016 | Deterre et al. |
| 9,522,276 | B2 | 12/2016 | Shen et al. |
| 9,522,280 | B2 | 12/2016 | Fishler et al. |
| 9,526,522 | B2 | 12/2016 | Wood et al. |
| 9,526,891 | B2 | 12/2016 | Eggen et al. |
| 9,526,909 | B2 | 12/2016 | Stahmann et al. |
| 9,533,163 | B2 | 1/2017 | Klimovitch et al. |
| 9,561,382 | B2 | 2/2017 | Persson et al. |
| 9,566,012 | B2 | 2/2017 | Greenhut et al. |
| 9,636,511 | B2 | 5/2017 | Carney et al. |
| 9,669,223 | B2 | 6/2017 | Auricchio et al. |
| 9,687,654 | B2 | 6/2017 | Sheldon et al. |
| 9,687,655 | B2 | 6/2017 | Pertijs et al. |
| 9,687,659 | B2 | 6/2017 | Von Arx et al. |
| 9,694,186 | B2 | 7/2017 | Carney et al. |
| 9,782,594 | B2 | 10/2017 | Stahmann et al. |
| 9,782,601 | B2 | 10/2017 | Ludwig |
| 9,789,317 | B2 | 10/2017 | Greenhut et al. |
| 9,789,319 | B2 | 10/2017 | Sambelashvili |
| 9,808,617 | B2 | 11/2017 | Ostroff et al. |
| 9,808,628 | B2 | 11/2017 | Sheldon et al. |
| 9,808,631 | B2 | 11/2017 | Maile et al. |
| 9,808,632 | B2 | 11/2017 | Reinke et al. |
| 9,808,633 | B2 | 11/2017 | Bonner et al. |
| 9,808,637 | B2 | 11/2017 | Sharma et al. |
| 9,855,414 | B2 | 1/2018 | Marshall et al. |
| 9,855,430 | B2 | 1/2018 | Ghosh et al. |
| 9,855,435 | B2 | 1/2018 | Sahabi et al. |
| 9,861,815 | B2 | 1/2018 | Tran et al. |
| 10,080,887 | B2 | 9/2018 | Schmidt et al. |
| 10,080,888 | B2 | 9/2018 | Kelly et al. |
| 10,080,900 | B2 | 9/2018 | Ghosh et al. |
| 10,080,903 | B2 | 9/2018 | Willis et al. |
| 10,086,206 | B2 | 10/2018 | Sambelashvili |
| 10,118,026 | B2 | 11/2018 | Grubac et al. |
| 10,124,163 | B2 | 11/2018 | Ollivier et al. |
| 10,124,175 | B2 | 11/2018 | Berthiaume et al. |
| 10,130,821 | B2 | 11/2018 | Grubac et al. |
| 10,137,305 | B2 | 11/2018 | Kane et al. |
| 10,201,710 | B2 | 2/2019 | Jackson et al. |
| 10,207,115 | B2 | 2/2019 | Echt et al. |
| 10,207,116 | B2 | 2/2019 | Sheldon et al. |
| 10,226,197 | B2 | 3/2019 | Reinke et al. |
| 10,226,639 | B2 | 3/2019 | Zhang |
| 10,232,182 | B2 | 3/2019 | Hareland et al. |
| 10,265,503 | B2 | 4/2019 | Schmidt et al. |
| 10,265,534 | B2 | 4/2019 | Greenhut et al. |
| 10,271,752 | B2 | 4/2019 | Regnier et al. |
| 10,278,601 | B2 | 5/2019 | Greenhut et al. |
| 10,279,165 | B2 | 5/2019 | Seifert et al. |
| 10,286,221 | B2 | 5/2019 | Sawchuk |
| 10,307,598 | B2 | 6/2019 | Ciciarelli et al. |
| 10,328,274 | B2 | 6/2019 | Zhang et al. |
| 10,342,981 | B2 | 7/2019 | Ghosh et al. |
| 2002/0032470 | A1 | 3/2002 | Linberg |
| 2002/0035376 | A1 | 3/2002 | Bardy et al. |
| 2002/0035377 | A1 | 3/2002 | Bardy et al. |
| 2002/0035378 | A1 | 3/2002 | Bardy et al. |
| 2002/0035380 | A1 | 3/2002 | Rissmann et al. |
| 2002/0035381 | A1 | 3/2002 | Bardy et al. |
| 2002/0042629 | A1 | 4/2002 | Bardy et al. |
| 2002/0042630 | A1 | 4/2002 | Bardy et al. |
| 2002/0042634 | A1 | 4/2002 | Bardy et al. |
| 2002/0049475 | A1 | 4/2002 | Bardy et al. |
| 2002/0052636 | A1 | 5/2002 | Bardy et al. |
| 2002/0068958 | A1 | 6/2002 | Bardy et al. |
| 2002/0072773 | A1 | 6/2002 | Bardy et al. |
| 2002/0082665 | A1 | 6/2002 | Haller et al. |
| 2002/0091414 | A1 | 7/2002 | Bardy et al. |

(56) References Cited

U.S. PATENT DOCUMENTS

| | | |
|---|---|---|
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 11/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0179541 A1 | 8/2007 | Prakash et al. |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239210 A1 | 10/2007 | Libbus et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171404 A1 | 7/2009 | Irani et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |

(56) References Cited

U.S. PATENT DOCUMENTS

| | | |
|---|---|---|
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0069983 A1 | 3/2010 | Peacock, III et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0298841 A1 | 11/2010 | Prinzen et al. |
| 2010/0312309 A1 | 12/2010 | Harding |
| 2010/0317978 A1 | 12/2010 | Maile et al. |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0270341 A1 | 11/2011 | Ruben et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0245665 A1 | 9/2012 | Friedman et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0289776 A1 | 11/2012 | Keast et al. |
| 2012/0289815 A1 | 11/2012 | Keast et al. |
| 2012/0290021 A1 | 11/2012 | Saurkar et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2012/0330392 A1 | 12/2012 | Regnier et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0131750 A1 | 5/2013 | Stadler et al. |
| 2013/0138006 A1 | 5/2013 | Bornzin et al. |
| 2013/0150639 A1 | 6/2013 | Diehl et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0165986 A1 | 6/2013 | Ghosh et al. |
| 2013/0184776 A1 | 7/2013 | Shuros et al. |
| 2013/0192611 A1 | 8/2013 | Taepke, II et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253309 A1 | 9/2013 | Allan et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |

(56) References Cited

U.S. PATENT DOCUMENTS

| | | |
|---|---|---|
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018690 A1 | 1/2014 | Carlson et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100624 A1 | 4/2014 | Ellingson |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0213916 A1 | 7/2014 | Doan et al. |
| 2014/0214104 A1 | 7/2014 | Greenhut et al. |
| 2014/0222015 A1 | 8/2014 | Keast et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0343348 A1 | 11/2014 | Kaplan et al. |
| 2014/0371818 A1 | 12/2014 | Bond et al. |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0091415 A1 | 4/2015 | Deterre et al. |
| 2015/0105836 A1 | 4/2015 | Bonner et al. |
| 2015/0126854 A1 | 5/2015 | Keast et al. |
| 2015/0142069 A1* | 5/2015 | Sambelashvili ...... A61N 1/3688 607/18 |
| 2015/0157861 A1 | 6/2015 | Aghassian |
| 2015/0157866 A1 | 6/2015 | Demmer et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0217123 A1 | 8/2015 | Deterre et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0230699 A1 | 8/2015 | Berul et al. |
| 2015/0238769 A1 | 8/2015 | Demmer et al. |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306401 A1 | 10/2015 | Demmer et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335884 A1 | 11/2015 | Khairkhahan et al. |
| 2015/0342466 A1 | 12/2015 | Thakur et al. |
| 2015/0360041 A1 | 12/2015 | Stahmann et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0051823 A1 | 2/2016 | Maile et al. |
| 2016/0067486 A1 | 3/2016 | Brown et al. |
| 2016/0067490 A1 | 3/2016 | Carney et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0144192 A1 | 5/2016 | Sanghera et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0028203 A1 | 2/2017 | Ghosh |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0112390 A1 | 4/2017 | Cho et al. |
| 2017/0189681 A1 | 7/2017 | Anderson |
| 2017/0274213 A1 | 9/2017 | Ghosh et al. |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |
| 2018/0008829 A1 | 1/2018 | An et al. |
| 2018/0021567 A1 | 1/2018 | An et al. |
| 2018/0021581 A1 | 1/2018 | An et al. |

(56) References Cited

U.S. PATENT DOCUMENTS

| | | |
|---|---|---|
| 2018/0021582 A1 | 1/2018 | An et al. |
| 2018/0256902 A1 | 9/2018 | Toy et al. |
| 2018/0256909 A1 | 9/2018 | Smith et al. |
| 2018/0264262 A1 | 9/2018 | Haasl et al. |
| 2018/0264270 A1 | 9/2018 | Koop et al. |
| 2018/0264272 A1 | 9/2018 | Haasl et al. |
| 2018/0264273 A1 | 9/2018 | Haasl et al. |
| 2018/0264274 A1 | 9/2018 | Haasl et al. |
| 2018/0339160 A1 | 11/2018 | Carroll |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 2030564 A2 | 3/2009 |
| EP | 1904166 B1 | 6/2011 |
| EP | 2471449 A1 | 4/2012 |
| EP | 2471452 A1 | 7/2012 |
| EP | 2433675 B1 | 1/2013 |
| EP | 2441491 B1 | 1/2013 |
| EP | 2639845 A1 | 9/2013 |
| EP | 2452721 B1 | 11/2013 |
| EP | 2662113 A3 | 11/2013 |
| EP | 1948296 B1 | 1/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 5/2002 |
| WO | 02098282 A2 | 12/2002 |
| WO | 2005000206 A3 | 1/2005 |
| WO | 2005042089 A1 | 5/2005 |
| WO | 2006065394 A1 | 6/2006 |
| WO | 2006069215 A2 | 6/2006 |
| WO | 2006086435 A3 | 8/2006 |
| WO | 2006113659 A1 | 10/2006 |
| WO | 2006124833 A3 | 11/2006 |
| WO | 2007073435 A1 | 6/2007 |
| WO | 2007075974 A2 | 7/2007 |
| WO | 2008034005 A2 | 3/2008 |
| WO | 2009006531 A1 | 1/2009 |
| WO | 2012054102 A1 | 4/2012 |
| WO | 2013080038 A2 | 6/2013 |
| WO | 2013098644 A3 | 7/2013 |
| WO | 2013184787 A1 | 12/2013 |
| WO | 2014120769 A1 | 8/2014 |
| WO | 2014178035 A1 | 11/2014 |
| WO | 2016014352 A1 | 1/2016 |

OTHER PUBLICATIONS

International Search Report and Written Opinion for Application No. PCT/US2019/012182, 11 pages, dated Mar. 11, 2019.
"Instructions for Use System 1, Leadless Cardiac Pacemaker (LCP) and Delivery Catheter," Nanostim Leadless Pacemakers, pp. 1-28, 2013.
Hachisuka et al., "Development and Performance Analysis of an Intra-Body Communication Device," The 12th International Conference on Solid State Sensors, Actuators and Microsystems, vol. 4A1.3, pp. 1722-1725, 2003.
Seyedi et al., "A Survey on Intrabody Communications for Body Area Network Application," IEEE Transactions on Biomedical Engineering, vol. 60(8): 2067-2079, 2013.
Spickler et al., "Totally Self-Contained Intracardiac Pacemaker," Journal of Electrocardiology, vol. 3(3&4): 324-331, 1970.
Wegmüller, "Intra-Body Communication for Biomedical Sensor Networks," Diss. ETH, No. 17323, 1-173, 2007.
International Search Report and Written Opinion for Application No. PCT/US2018/046885, 22 pages, dated Nov. 15, 2018.
International Search Report and Written Opinion for Application No. PCT/US2018/062631, 13 pages, dated Feb. 5, 2019.
International Search report and Written Opinion for Application No. PCT/US2018/063131, 24 pages, dated Jan. 24, 2019.
International Search Report and Wriitten Opinion for Application No. PCT/US2018/062469, 12 pages, dated Feb. 26, 2019.
International Search Report and Written Opinion for Application No. PCT/US2018/063122, 14 pages, dated Feb. 14, 2019.
Liang, "Piezolectric Pressure Pressure Sensors Based on Flexible PZT Thick-Film Composite Device", University of Pittsburg, 2014, 87 pages.
Chinitz et al, "Accelometer-Based Atrioventricular Synchronus Pacing with a Ventricular Leadless Pacemaker: Results from the Micra Atrioventricular Feasibility Studies", Heart Rhythm, vol. 15, 2018, pp. 1363-1371.

* cited by examiner

DUAL CHAMBER PACING WITHOUT BEAT-TO-BEAT COMMUNICATION

CROSS REFERENCE TO RELATED APPLICATIONS

This application claims the benefit of U.S. Provisional Patent Application Ser. No. 62/613,598 filed on Jan. 4, 2018, the disclosure of which is incorporated herein by reference.

TECHNICAL FIELD

The present disclosure generally relates to implantable medical devices, and more particularly, to systems that use one or more leadless cardiac pacemaker(s) for monitoring, pacing and/or defibrillating a patient's heart.

BACKGROUND

Implantable medical devices are commonly used today to monitor a patient and/or deliver therapy to a patient. For example, and in some instances, pacing devices are used to treat patients suffering from various heart conditions that may result in a reduced ability of the heart to deliver sufficient amounts of blood to a patient's body. Such heart conditions may lead to slow, rapid, irregular, and/or inefficient heart contractions. To help alleviate some of these conditions, various medical devices (e.g., pacemakers, defibrillators, etc.) can be implanted in a patient's body. Such devices may monitor and in some cases provide electrical stimulation (e.g. pacing, defibrillation, etc.) to the heart to help the heart operate in a more normal, efficient and/or safe manner. In some cases, it may be beneficial to detect cardiac events occurring in multiple chambers of the heart and/or provide therapy in multiple chambers of the heart. In some cases, this may be used to enhance the effectiveness of the cardiac pacing therapy and/or may allow different types of cardiac pacing therapy to be delivered.

SUMMARY

This disclosure generally relates to implantable medical devices, and more particularly, to systems that use a leadless cardiac pacemaker for monitoring, pacing and/or defibrillating a patient's heart.

In a first example of the disclosure, a leadless cardiac pacemaker (LCP) system may be configured to sense cardiac activity and to deliver pacing therapy to a patient's heart. The LCP system may include a first LCP configured to be positioned in a first chamber of a heart (e.g. ventricle) and to deliver a first pacing therapy to the first chamber of the heart, and a second LCP configured to be positioned in the second chamber of the heart (e.g. atrium) and to deliver a second pacing therapy to the second chamber of the heart. The first LCP may include a housing, a first electrode secured relative to the housing and exposed to the environment outside of the housing, a second electrode secured relative to the housing and exposed to the environment outside of the housing, a sensing module configured to detect a cardiac event of a second chamber of the heart (e.g. atrium) and generate a corresponding first timing fiducial, and a control module operatively coupled to the first electrode, the second electrode, and the sensing module of the first LCP. The second LCP may include a housing, a first electrode secured relative to the housing and exposed to the environment outside of the housing, a second electrode secured relative to the housing and exposed to the environment outside of the housing, a sensing module configured to detect a cardiac event of the first chamber and/or the second chamber of the heart, and a control module operatively coupled to the first electrode, the second electrode, and the sensing module of the second LCP. The control module of the first LCP may be configured to time the delivery of at least part of the first pacing therapy of the first LCP based, at least in part, on the first timing fiducial.

Alternatively or additionally to the above example, the first pacing therapy delivered by the first LCP in the first chamber may be synchronized with the second chamber of the heart based, at least in part, on the first timing fiducial.

Alternatively or additionally to any of the examples above, in another example, the first LCP and the second LCP may be configured to wirelessly communicate with each other, and wherein when the first timing fiducial is of insufficient quality the first pacing therapy delivered by the first LCP in the first chamber is synchronized with the second chamber of the heart via a communication between the second LCP and the first LCP.

Alternatively or additionally to any of the examples above, in another example, the first timing fiducial may be considered to be of insufficient quality when the cardiac event was not detected, the signal to noise ratio (SNR) of the detected cardiac event is below a SNR threshold, a detected heart rate in the first and/or second chamber is above a heart rate threshold, or a detected pacing rate in the first and/or second chamber is above a pacing rate threshold.

Alternatively or additionally to any of the examples above, in another example, the first LCP and the second LCP may be configured to wirelessly communicate with each other using conducted communication.

Alternatively or additionally to any of the examples above, in another example, the first chamber may be the right ventricle of the heart and the second chamber may be the right atrium of the heart.

Alternatively or additionally to any of the examples above, in another example, the sensing module of the first LCP may include an electrical signal sensor and a pressure sensor.

Alternatively or additionally to any of the examples above, in another example, the sensing module of the first LCP may include an electrical signal sensor and an accelerometer.

Alternatively or additionally to any of the examples above, in another example, the cardiac event of the second chamber may include one or more of an atrial pressure wave, an atrial electrical P-signal, and an atrial pace pulse.

Alternatively or additionally to any of the examples above, in another example, the first pacing therapy may include a VVI or VDD pacing therapy, and the second pacing therapy may include an AAI or ADD pacing therapy.

Alternatively or additionally to any of the examples above, in another example, the second LCP may be configured to detect atrial fibrillation, and when the second LCP detects atrial fibrillation the second LCP is configured to wirelessly communicate with the first LCP to switch the first LCP to a VVI pacing therapy.

Alternatively or additionally to any of the examples above, in another example, the second LCP may be configured to detect when an atrial fibrillation resolves, and when the second LCP detects that an atrial fibrillation resolves, the second LCP is configured to wirelessly communicate with the first LCP to switch the first LCP to a VDD pacing therapy.

Alternatively or additionally to any of the examples above, in another example, the first chamber may be the right atrium of the heart and the second chamber may be the right ventricle of the heart.

Alternatively or additionally to any of the examples above, in another example, the cardiac event may include one or more of a ventricle electrical R-signal and a ventricle pace pulse.

Alternatively or additionally to any of the examples above, in another example, the first pacing therapy may include an AAI or ADD pacing therapy, and the second pacing therapy may include a VVI or VDD pacing therapy.

In another example, a leadless cardiac pacemaker (LCP) system may be configured to sense cardiac activity and to deliver pacing therapy to a patient's heart. The LCP system may include a first LCP configured to be positioned in a ventricle of a heart and a second LCP configured to be positioned in an atrium of the heart. The first LCP may be configured to detect a cardiac event of the atrium of the heart and generate a corresponding atrial timing fiducial and the first LCP may be configured to deliver a pacing therapy to the ventricle of the heart. The pacing therapy delivered by the first LCP in the ventricle may be synchronized with the atrium of the heart using the atrial timing fiducial.

Alternatively or additionally to any of the examples above, in another example, the first LCP and the second LCP may be configured to wirelessly communicate with each other by conducted communication, and wherein when the atrial timing fiducial is of insufficient quality the pacing therapy delivered by the first LCP in the ventricle is synchronized with the atrium of the heart via a communication between the second LCP and the first LCP.

Alternatively or additionally to any of the examples above, in another example, the first timing fiducial may be of insufficient quality when the cardiac event was not detected, the signal to noise ratio (SNR) of the detected cardiac event is below a SNR threshold, a detected heart rate is above a heart rate threshold, or a detected pacing rate is above a heart rate threshold.

In another example, a leadless cardiac pacemaker (LCP) system may be configured to sense cardiac activity and to deliver pacing therapy to a patient's heart. The LCP system may include a first LCP configured to be positioned in an atrium of a heart and a second LCP configured to be positioned in a ventricle of the heart. The first LCP may be configured to detect a cardiac event of the ventricle of the heart and generate a corresponding ventricular timing fiducial and the first LCP may be configured to deliver a pacing therapy to the atrium of the heart. The pacing therapy delivered by the first LCP in the atrium may be synchronized with the ventricle of the heart using the ventricular timing fiducial.

Alternatively or additionally to any of the examples above, in another example, the first LCP and the second LCP may be configured to wirelessly communicate with each other by conducted communication, and wherein when the ventricular timing fiducial is of insufficient quality the pacing therapy delivered by the first LCP in the atrium is synchronized with the ventricle of the heart via a communication between the second LCP and the first LCP.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
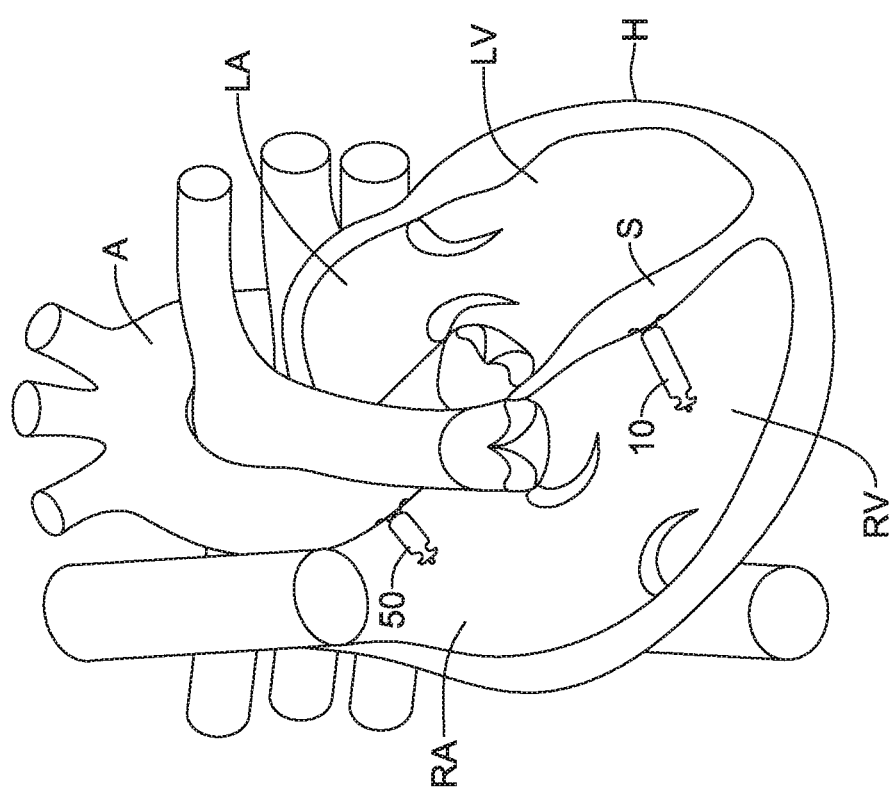
FIG. 1 is a plan view of example leadless pacing devices implanted within a heart.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure. While the present disclosure is applicable to any suitable implantable medical device (IMD), the description below uses pacemakers and more particularly leadless cardiac pacemakers (LCP) as particular examples.

All numbers are herein assumed to be modified by the term "about", unless the content clearly dictates otherwise. The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is contemplated that the feature, structure, or characteristic may be applied to other embodiments whether or not explicitly described unless clearly stated to the contrary.

A normal, healthy heart induces contraction by conducting intrinsically generated electrical signals throughout the heart. These intrinsic signals cause the muscle cells or tissue of the heart to contract in a coordinated manner. These contractions force blood out of and into the heart, providing circulation of the blood throughout the rest of the body. Many patients suffer from cardiac conditions that affect the efficient operation of their hearts. For example, some hearts develop diseased tissue that no longer generate or efficiently conduct intrinsic electrical signals. In some examples, diseased cardiac tissue may conduct electrical signals at differing rates, thereby causing an unsynchronized and inefficient contraction of the heart. In other examples, a heart may generate intrinsic signals at such a low rate that the heart rate becomes dangerously low. In still other examples, a heart may generate electrical signals at an unusually high rate, even resulting in cardiac fibrillation. In some cases such an abnormality can develop into a fibrillation state, where the contraction of the patient's heart chambers are almost completely de-synchronized and the heart pumps very little to no blood. Implantable medical devices, which may be configured to determine occurrences of such cardiac abnormalities or arrhythmias and deliver one or more types of electrical stimulation therapy to patient's hearts, may help to terminate or alleviate these and other cardiac conditions.

It is contemplated that atrial events or artifacts indicative of an atrial event may be used by a device implanted in the right (or left) ventricle to time a pacing pulse for the ventricle in support of treating bradycardia events. In some cases, the timing of the ventricle pacing pulse may be adjusted to maximize the amount of blood entering the right ventricle through passive filling. In some instances, this may include adjusting an AV delay relative to an atrial fiducial (e.g., atrial kick). In some cases, a measured pressure change (or other atrial fiducial) over time may be used to support management of a CRT cardiac therapy (e.g., if placed in the left ventricle), patient health status monitoring and/or any other suitable goal. It is contemplated that measuring events in one of or both of the ventricle and atrium using a single leadless cardiac pacemaker may replicate a dual chamber system using only a single device. For example, such a system may enable a device to be positioned in a ventricle and capable of sensing intrinsic ventricular and atrial events and pacing the ventricle when appropriate (e.g., a VDD pacemaker).

In some cases, it may be desirable to position a device within both the right ventricle and the right atrium (e.g. to provide a dual chamber pacing system), or other chamber combinations. Dual chamber pacing is currently accomplished using transvenous pacemakers. However, dual chamber leadless pacing may have many advantageous including, but not limited to, the lack of a device pocket, fewer infections, the ability to add leadless pacemakers in a modular fashion, etc. However, beat-to-beat communication (i.e. a communication for each and every heart beat whenever therapy is being delivered) between two implanted devices may use a significant amount of energy, requiring larger battery and increased device size, and may be complicated to implement.

In some cases, and in one example, it may be desirable to provide a dual leadless pacemaker system capable of pacing in an atrium (for example, the right atrium) and a ventricle (for example, the right ventricle) without the need for beat-to-beat communication whenever therapy is being delivered. In some cases, the ventricular leadless pacemaker may be configured to detect atrial activity from the ventricle and synchronize the ventricular pacing therapy with the atrium beats based on the detected atrial activity. If the ventricular leadless cardiac pacemaker temporarily fails to detect atrial activity because of noise, posture, patient activity or for any other reason, the atrial leadless cardiac pacemaker may be configured to communicate atrial events to the ventricular leadless cardiac pacemaker and the ventricular leadless cardiac pacemaker may synchronize the ventricular pacing therapy with the atrial beats based on those communications. More generally, and in another example, it may be desirable to provide a dual device system that includes a first device in the atrium that can sense atrial activity that is in selectively communication with a leadless cardiac pacemaker implanted in the ventricle. The leadless cardiac pacemaker in the ventricle may be capable of sensing atrial and ventricle activity from the ventricle, and may pace the ventricle. If the leadless cardiac pacemaker temporarily fails to detect atrial activity because of noise, posture, patient activity or for any other reason, the first device may be configured to communicate atrial events to the leadless cardiac pacemaker, and the leadless cardiac pacemaker may synchronize the ventricular pacing therapy with the atrial beats based on those communications. These are just a few examples.

FIG. 1 illustrates a first illustrative implantable leadless cardiac pacing device 10 (e.g., a leadless pacemaker) implanted in a chamber of a heart H, such as the right ventricle RV. FIG. 1 also illustrates a second example device 50 (e.g., a leadless pacemaker) in another chamber of the H, such as the right atrium RA. In some cases, the first device 10 may be affixed to the ventricular septum S as shown, the ventricle apex, or any other suitable locations. The left atrium LA, left ventricle LV, and aorta A of the Heart H are also illustrated. Although shown implanted in the right ventricle RV and right atrium RA, it is contemplated that the implantable devices 10, 50 may alternatively be implanted in any combination of the right ventricle RV, the right atrium RA, the left atrium LA, the left ventricle LV, or other cardiovascular location, as desired. In some instances, both devices 10, 50 may be implanted in the same chamber.

Figure 2:
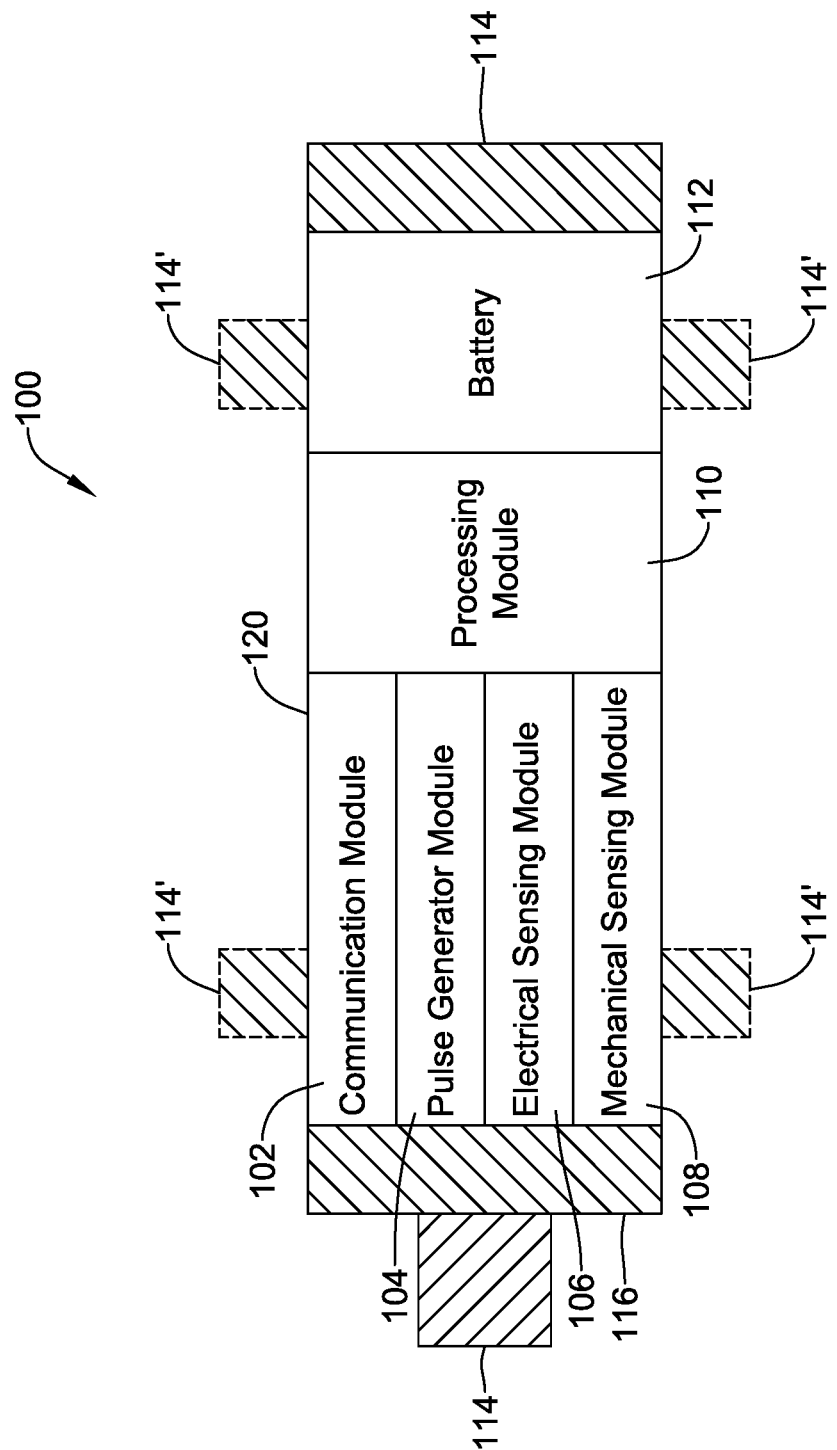
FIG. 2 is a schematic block diagram of an illustrative leadless cardiac pacemaker (LCP) according to one example of the present disclosure.

FIG. 2 depicts an illustrative leadless cardiac pacemaker (LCP) 100, such as LCP 10 or LCP 50, which may be implanted into a patient to provide bradycardia therapy, cardiac resynchronization therapy (CRT), anti-tachycardia pacing (ATP) therapy, defibrillation therapy, and/or the like. As can be seen in FIG. 2, the illustrative LCP 100 may be a compact device with all components housed within and/or on the LCP housing 120. In the example shown in FIG. 2, the LCP 100 includes a communication module 102, a pulse generator module 104, an electrical sensing module 106, a mechanical sensing module 108, a processing module 110, a battery 112, and electrodes 114. It is contemplated that the LCP 100 may include more or fewer modules, depending on the application.

The communication module 102 may be configured to communicate with remote devices such as sensors, other devices, and/or the like, that are located externally and/or internally to the patient's body. The other devices may be primarily functioning as a medical device (e.g. a LCP programmer, an implanted sensor) or a device primarily functioning as a non-medical device (e.g. a personal computer, tablet computer, smart phone, laptop computer or the like). Irrespective of the location or primary function, the remote devices (i.e., external to the LCP 100 but not necessarily external to the patient's body) may communicate with the LCP 100 via the communication module 102 to accomplish one or more desired functions. For example, the LCP 100 may communicate information, such as sensed signals, data, instructions, messages, etc., to a remote medical device through the communication module 102. The remote medical device may then use the communicated signals, data, instructions and/or messages to perform various functions, such as determining occurrences of arrhythmias, delivering electrical stimulation therapy, storing received data, analyzing received data, transmitting the received data to an external programmer or server or the like for review by a physician, and/or performing any other suitable function. The LCP 100 may additionally or alternatively receive information such as signals, timing fiducials, data, instructions and/or messages from the remote medical device through the communication module 102, and the LCP 100 may use the received signals, timing fiducials, data, instructions and/or messages to perform various functions, such as determining occurrences of arrhythmias, delivering electrical stimulation therapy, storing received data, analyzing received data, and/or performing any other suitable function. The communication module 102 may be configured to use one or more methods for communicating with remote devices. For example, the communication module 102 may communicate via radiofrequency (RF) signals, inductive coupling, optical signals, acoustic signals, conducted communication signals, and/or any other signals suitable for communication.

In the example shown in FIG. 2, the pulse generator module 104 may be electrically connected to the electrodes 114. In some examples, the LCP 100 may include one or more additional electrodes 114'. In such examples, the pulse generator 104 may also be electrically connected to the additional electrodes 114'. The pulse generator module 104 may be configured to generate electrical stimulation signals. For example, the pulse generator module 104 may generate electrical stimulation signals by using energy stored in a battery 112 within the LCP 100 and deliver the generated electrical stimulation signals via the electrodes 114 and/or 114'. Alternatively, or additionally, the pulse generator 104 may include one or more capacitors, and the pulse generator 104 may charge the one or more capacitors by drawing energy from the battery 112. The pulse generator 104 may then use the energy of the one or more capacitors to deliver the generated electrical stimulation signals via the electrodes 114 and/or 114'. In at least some examples, the pulse generator 104 of the LCP 100 may include switching circuitry to selectively connect one or more of the electrodes 114 and/or 114' to the pulse generator 104 in order to select which of the electrodes 114/114' (and/or other electrodes) that the pulse generator 104 uses to deliver the electrical stimulation therapy. The pulse generator module 104 may generate electrical stimulation signals with particular features or in particular sequences in order to provide one or multiple of a number of different stimulation therapies. For example, the pulse generator module 104 may be configured to generate electrical stimulation signals to provide electrical stimulation therapy to combat bradycardia, tachycardia, cardiac dyssynchrony, bradycardia arrhythmias, tachycardia arrhythmias, fibrillation arrhythmias, cardiac synchronization arrhythmias and/or to produce any other suitable electrical stimulation therapy. Some more common electrical stimulation therapies include bradycardia therapy, anti-tachycardia pacing (ATP) therapy, cardiac resynchronization therapy (CRT), and cardioversion/defibrillation therapy.

In some examples, the LCP 100 may not include a pulse generator 104 or may turn off the pulse generator 104. When so provided, the LCP 100 may be a diagnostic and/or sensor only device. In such examples, the LCP 100 may not deliver electrical stimulation therapy to a patient. Rather, the LCP 100 may collect data about cardiac electrical activity and/or other physiological parameters of the patient and communicate such data and/or determinations to one or more other medical devices via the communication module 102. In some cases, the data may include timing fiducials associated with certain cardiac events, such as cardiac events that are associated with the contraction of a chamber of the heart.

In some examples, the LCP 100 may include an electrical sensing module 106, and in some cases, a mechanical sensing module 108. The electrical sensing module 106 may be configured to sense the cardiac electrical activity of the heart. For example, the electrical sensing module 106 may be connected to the electrodes 114/114', and the electrical sensing module 106 may be configured to receive cardiac electrical signals conducted through the electrodes 114/114'. The cardiac electrical signals may represent local information from the chamber (e.g., near field) in which the LCP 100 is implanted and/or remote information from a chamber (e.g., far field) in which the LCP 100 is not implanted. For instance, if the LCP 100 is implanted within a ventricle of the heart, cardiac electrical signals sensed by the LCP 100 through the electrodes 114/114' may represent ventricular cardiac electrical signals (e.g. near field signals), and possibly some weaker atrial electrical signals (e.g. far field signals). The electrical sensing module 106 may be configured to detect voltage, current and/or impedance. An electrogram sensing module (not explicitly shown) may be provided as a part of the electrical sensing module, if desired.

The mechanical sensing module 108 may include one or more sensors, such as an accelerometer, a gyroscope, a microphone, a hydrophone, a blood pressure sensor, a heart sound sensor, a blood-oxygen sensor, a temperature sensor, a flow sensor, a strain sensor, and/or any other suitable sensors that are configured to measure or sense one or more mechanical and/or chemical parameters of the patient. In some cases, the mechanical sensing module 108 may include two or more of a pressure measurement module, an acoustic measurement module, and an acceleration measurement module.

Both the electrical sensing module 106 and the mechanical sensing module 108 may be connected to a processing module 110, which may provide signals representative of the sensed mechanical parameters. Although described with respect to FIG. 2 as separate sensing modules, in some cases, the electrical sensing module 106 and the mechanical sensing module 108 may be combined into a single sensing module, as desired.

The electrodes 114/114' can be secured relative to the housing 120 but may be exposed to the tissue and/or blood surrounding the LCP 100. In some cases, the electrodes 114 may be generally disposed on or near either end of the LCP 100 and may be in electrical communication with one or more of the modules 102, 104, 106, 108, and 110. The electrodes 114/114' may be supported by the housing 120, although in some examples, the electrodes 114/114' may be spaced from the housing 120 and secured relative to the housing 120 through short connecting wires (e.g., tail). In examples where the LCP 100 includes one or more electrodes 114', the electrodes 114' may in some cases be disposed on the sides of the housing 120 of the LCP 100, which may increase the number of electrodes by which the LCP 100 may sense cardiac electrical activity, deliver electrical stimulation and/or communicate with an external medical device. The electrodes 114/114' can be made up of one or more biocompatible conductive materials such as various metals or alloys that are known to be safe for implantation within a human body. In some instances, the electrodes 114/114' connected to LCP 100 may have an insulative portion that electrically isolates the electrodes 114/114' from adjacent electrodes, the housing 120, and/or other parts of the LCP 100.

The processing or control module 110 can be configured to control the operation of the LCP 100. For example, the processing module 110 may be configured to receive electrical signals from the electrical sensing module 106 and/or the mechanical sensing module 108. Based on the received signals, the processing module 110 may determine, for example, a need for pacing therapy such as bradycardia therapy, cardiac resynchronization therapy (CRT), anti-tachycardia pacing (ATP) therapy, defibrillation therapy, and/or the like. The processing module 110 may control the pulse generator module 104 to generate electrical stimulation in accordance with one or more pacing therapies. The processing module 110 may further receive information from the communication module 102. In some examples, the processing module 110 may use such received information to help determine the need for pacing therapy and/or what type of pacing therapy. The processing module 110 may additionally control the communication module 102 to send/receive information to/from other devices.

In some examples, the processing module 110 may include a pre-programmed chip, such as a very-large-scale integration (VLSI) chip and/or an application specific integrated circuit (ASIC). In such embodiments, the chip may be pre-programmed with control logic in order to control the operation of the LCP 100. By using a pre-programmed chip, the processing module 110 may use less power than other programmable circuits (e.g., general purpose programmable microprocessors) while still being able to maintain basic functionality, thereby potentially increasing the battery life of the LCP 100. In other examples, the processing module 110 may include a programmable microprocessor. Such a programmable microprocessor may allow a user to modify the control logic of the LCP 100 even after implantation, thereby allowing for greater flexibility of the LCP 100 than when using a pre-programmed ASIC. In some examples, the processing module 110 may further include a memory, and the processing module 110 may store information on and read information from the memory. In other examples, the LCP 100 may include a separate memory (not shown) that is in communication with the processing module 110, such that the processing module 110 may read and write information to and from the separate memory.

The battery 112 may provide power to the LCP 100 for its operations. In some examples, the battery 112 may be a non-rechargeable lithium-based battery. In other examples, a non-rechargeable battery may be made from other suitable materials, as desired. Because the LCP 100 is an implantable device, access to the LCP 100 may be limited after implantation. Accordingly, it is desirable to have sufficient battery capacity to deliver therapy over a period of treatment such as days, weeks, months, years or even decades. In some instances, the battery 112 may a rechargeable battery, which may help increase the useable lifespan of the LCP 100. In still other examples, the battery 112 may be some other type of power source, as desired.

To implant the LCP 100 inside a patient's body, an operator (e.g., a physician, clinician, etc.), may fix the LCP 100 to the cardiac tissue of the patient's heart. To facilitate fixation, the LCP 100 may include one an anchor 116 (or fixation mechanism 414 shown in FIG. 6). The anchor 116 (or fixation mechanism 414) may include any one of a number of fixation or anchoring mechanisms. For example, the anchor 116 (or fixation mechanism 414) may include one or more pins, staples, threads, screws, helix, tines, and/or the like. In some examples, although not shown, the anchor 116 (or fixation mechanism 414) may include threads on its external surface that may run along at least a partial length of the anchor 116 (or fixation mechanism 414). The threads may provide friction between the cardiac tissue and the anchor to help fix the anchor 116 (or fixation mechanism 414) within the cardiac tissue. In other examples, the anchor 116 may include other structures such as barbs, spikes, or the like to facilitate engagement with the surrounding cardiac tissue.

Figure 3:
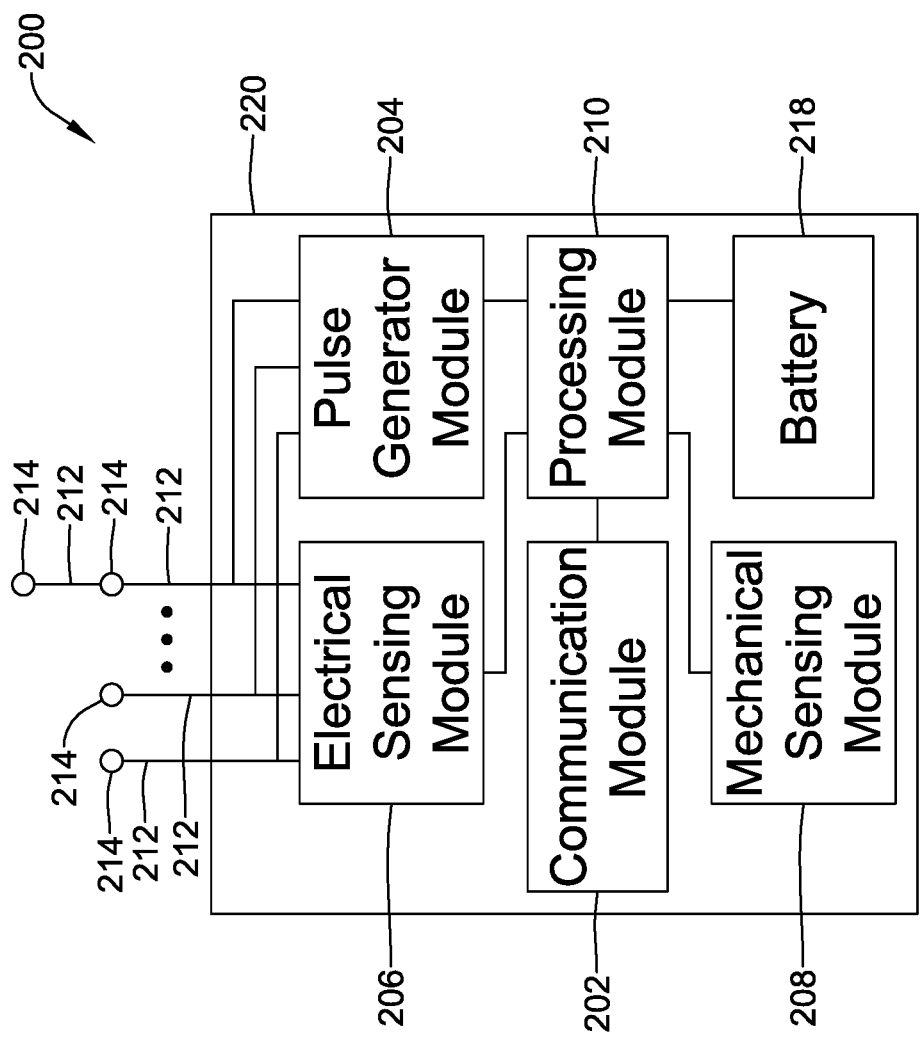
FIG. 3 a schematic block diagram of another medical device (MD), which may be used in conjunction with an LCP 100 (FIG. 2) in order to detect and/or treat cardiac arrhythmias and/or other heart conditions.

FIG. 3 depicts an example of another medical device (MD) 200, which may be used in conjunction with an LCP 100 (FIG. 2) in order to detect and/or treat cardiac arrhythmias and other heart conditions. In the example shown, the MD 200 may include a communication module 202, a pulse generator module 204, an electrical sensing module 206, a mechanical sensing module 208, a processing module 210, and a battery 218. Each of these modules may be similar to the modules 102, 104, 106, 108, and 110 of the LCP 100. Additionally, the battery 218 may be similar to the battery 112 of the LCP 100. In some examples, the MD 200 may have a larger volume within the housing 220 than LCP 100. In such examples, the MD 200 may include a larger battery and/or a larger processing module 210 capable of handling more complex operations than the processing module 110 of the LCP 100.

While it is contemplated that the MD 200 may be another leadless pacemaker device such as shown in FIG. 2, in some instances the MD 200 may include leads such as leads 212. The leads 212 may include electrical wires that conduct electrical signals between the electrodes 214 and one or more modules located within the housing 220. In some cases, the leads 212 may be connected to and extend away from the housing 220 of the MD 200. In some examples, the leads 212 are implanted on, within, or adjacent to a heart of a patient. The leads 212 may contain one or more electrodes 214 positioned at various locations on the leads 212, and in some cases at various distances from the housing 220. Some of the leads 212 may only include a single electrode 214, while other leads 212 may include multiple electrodes 214. Generally, the electrodes 214 are positioned on the leads 212 such that when the leads 212 are implanted within the patient, one or more of the electrodes 214 are positioned to perform a desired function. In some cases, the one or more of the electrodes 214 may be in contact with the patient's cardiac tissue. In some cases, the one or more of the electrodes 214 may be positioned sub sternally or subcutaneously and spaced from but adjacent to the patient's heart. In some cases, the electrodes 214 may conduct intrinsically generated electrical signals to the leads 212, e.g., signals representative of intrinsic cardiac electrical activity. The leads 212 may, in turn, conduct the received electrical signals to one or more of the modules 202, 204, 206, and 208 of the MD 200. In some cases, the MD 200 may generate electrical stimulation signals, and the leads 212 may conduct the generated electrical stimulation signals to the electrodes 214. The electrodes 214 may then conduct the electrical signals and deliver the signals to the patient's heart (either directly or indirectly).

The mechanical sensing module 208, as with the mechanical sensing module 108, may contain or be electrically connected to one or more sensors, such as microphones, hydrophones, accelerometers, gyroscopes, blood pressure sensors, heart sound sensors, blood-oxygen sensors, acoustic sensors, ultrasonic sensors, strain sensors, and/or other sensors which are configured to measure one or more mechanical/chemical parameters of the heart and/or patient. In some examples, one or more of the sensors may be located on the leads 212, but this is not required. In some examples, one or more of the sensors may be located in the housing 220.

While not required, in some examples, the MD 200 may be an implantable medical device. In such examples, the housing 220 of the MD 200 may be implanted in, for example, a transthoracic region of the patient. The housing 220 may generally include any of a number of known materials that are safe for implantation in a human body and may, when implanted, hermetically seal the various components of the MD 200 from fluids and tissues of the patient's body.

In some cases, the MD 200 may be an implantable cardiac pacemaker (ICP). In this example, the MD 200 may have one or more leads, for example leads 212, which are implanted on or within the patient's heart. The one or more leads 212 may include one or more electrodes 214 that are in contact with cardiac tissue and/or blood of the patient's heart. The MD 200 may be configured to sense intrinsically generated cardiac electrical signals and determine, for example, one or more cardiac arrhythmias based on analysis of the sensed signals. In some cases, the MD 200 may be configured to deliver CRT, ATP therapy, bradycardia therapy, and/or other therapy types via the leads 212 implanted within the heart or in concert with the LCP by commanding the LCP to pace and/or providing timing fiducials to the LCP. In some examples, the MD 200 may additionally be configured to provide defibrillation therapy.

In some instances, the MD 200 may be an implantable cardioverter-defibrillator (ICD). In such examples, the MD 200 may include one or more leads implanted within a patient's heart. The MD 200 may also be configured to sense cardiac electrical signals, determine occurrences of tachyarrhythmias based on the sensed signals, and may be configured to deliver defibrillation therapy in response to determining an occurrence of a tachyarrhythmia. In some instances, the MD 200 may be a subcutaneous implantable cardioverter-defibrillator (S-ICD). In examples where the MD 200 is an S-ICD, one of the leads 212 may be a subcutaneously or substernally implanted lead that is spaced from the heart. In at least some examples where the MD 200 is an S-ICD, the MD 200 may include only a single lead which is implanted subcutaneously or substernally, but this is not required. In some cases, the S-ICD lead may extend subcutaneously from the S-ICD can, around the sternum and may terminate adjacent the interior surface of the sternum and spaced from the heart.

In some examples, the MD 200 may not be an implantable medical device. Rather, the MD 200 may be a device external to the patient's body, and may include skin-electrodes that are placed on a patient's body. In such examples, the MD 200 may be able to sense surface electrical signals (e.g., cardiac electrical signals that are generated by the heart or electrical signals generated by a device implanted within a patient's body and conducted through the body to the skin). In such examples, the MD 200 may be configured to deliver various types of electrical stimulation therapy, including, for example, defibrillation therapy. The MD 200 may be further configured to help deliver electrical stimulation via the LCP by commanding the LCP to deliver the therapy and/or providing timing fiducials to the LCP.

It is contemplated that one or more LCPs 100 and/or one or more MDs 200 may be used in combination as an example medical device system. The various devices 100, 200 may communicate through various communication pathways including using RF signals, inductive coupling, conductive coupling optical signals, acoustic signals, or any other signals suitable for communication. The system may further include and be in communication with a display. The display may be a personal computer, tablet computer, smart phone, laptop computer, or other display as desired. In some instances, the display may include input means for receiving an input from a user. For example, the display may also include a keyboard, mouse, actuatable (e.g., pushable) buttons, or a touchscreen display. These are just examples. Some illustrative medical device systems are described in commonly assigned Patent Application No. 62/547,458, entitled IMPLANTABLE MEDICAL DEVICE WITH PRESSURE SENSOR and filed on Aug. 18, 2017, which is hereby incorporated by reference.

Figure 4:
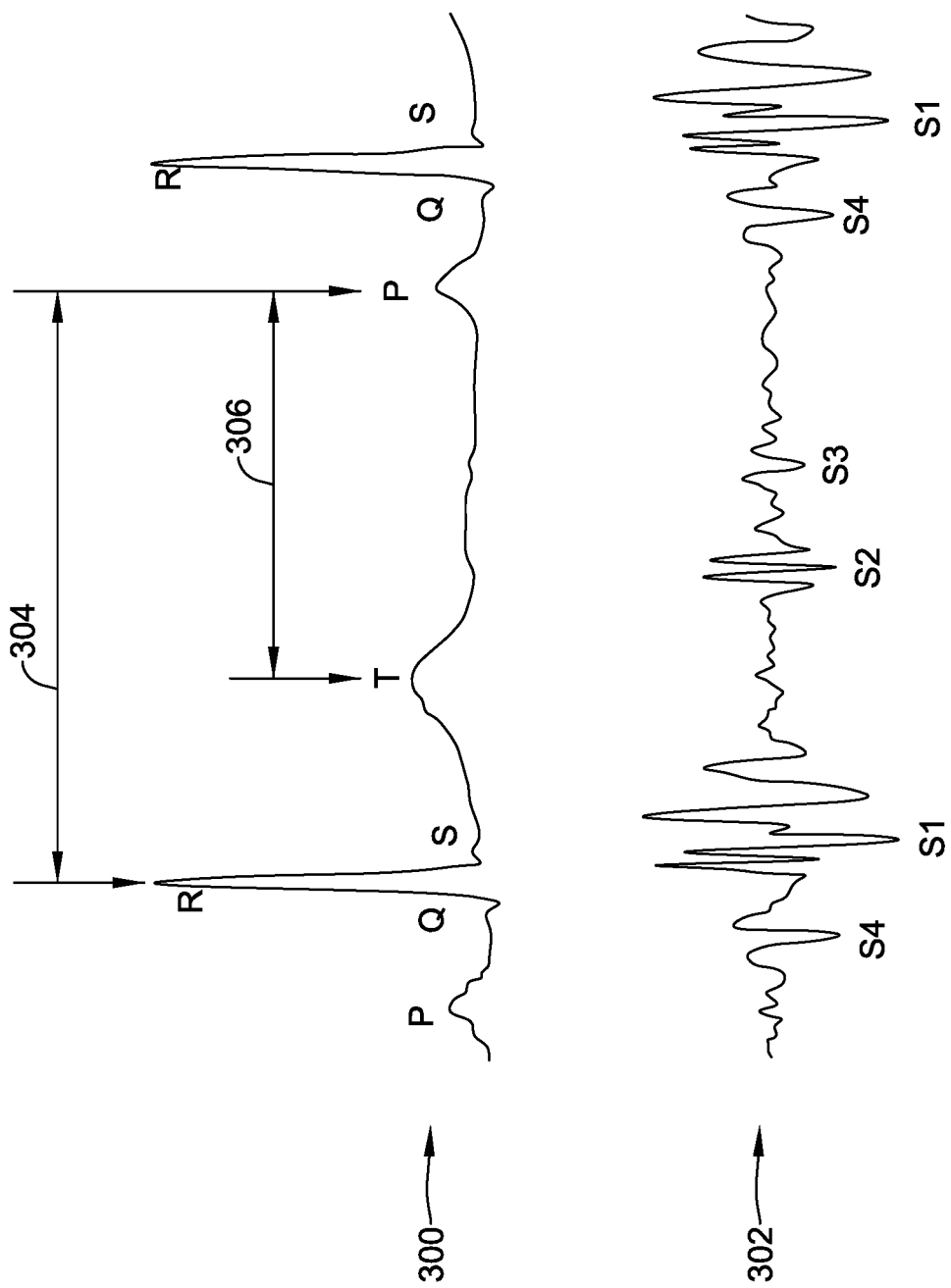
FIG. 4 is a graphical representation of an illustrative electrocardiogram (ECG) showing a temporal relationship between electrical signals of the heart and mechanical indications of contraction of the heart.

With reference to FIG. 4, it will be appreciated that a human heart is controlled via electrical signals that pass through the cardiac tissue and that can be detected by implanted devices such as but not limited to the LCP's 100 and/or MD's 200 of FIG. 2 or 3. FIG. 4 is a graphical representation of an illustrative electrocardiogram (ECG) 300 showing a temporal relationship between electrical signals of the heart and mechanical indications 302 of contraction of the heart (e.g., heart sounds). As can be seen in the illustrative ECG 300, a heartbeat includes a P-wave that indicates atrial depolarization associated with an atrial contraction to load the ventricles. A QRS complex, including a Q-wave, an R-wave and an S-wave, represents a ventricular depolarization that is associated with the ventricles contracting to pump blood to the body and lungs. A T-wave shows the repolarization of the ventricles in preparation for a next heartbeat. With heart disease, the timing of these individual events may be anomalous or abnormal, and the shape, amplitude and/or timing of the various waves can be different from that shown. It will be appreciated that the ECG 300 may be detected by implanted devices such as but not limited to the LCP 100 and/or MD 200 of FIG. 2 or 3.

The various cardiac events detectable via the ECG 300 can also be detected by the mechanical sensing module. A characteristic or event in the electrical signal (e.g., ECG 300) often has a corresponding mechanical response. The mechanical response is typically delayed because it takes some time for the heart to respond to the electrical signals.

It will be appreciated that heart sounds may be considered as an example of mechanical indications of a heart beating. Other illustrative mechanical indications may include, for example, endocardial acceleration or movement of a heart wall detected by an accelerometer in the LCP, acceleration or movement of a heart wall detected by an accelerometer in an SICD, a pressure, pressure change, or pressure change rate in a chamber of the heart detected by a pressure sensor of the LCP or other implantable device, acoustic signals caused by heart movements detected by an acoustic sensor (e.g., accelerometer, microphone, etc.), twisting of the heart detected by a gyroscope in the LCP or other implantable device, and/or any other suitable indication of a heart chamber beating.

Referring to FIG. 4, in some cases, there may be a first heart sound denoted S1 that is produced by vibrations generated by closure of the mitral and tricuspid valves during a ventricular contraction, a second heart sound denoted S2 that is produced by closure of the aortic and pulmonary valves, a third heart sound denoted S3 that is an early diastolic sound caused by the rapid entry of blood from the right atrium into the right ventricle and from the left atrium into the left ventricle, and a fourth heart sound denoted S4 that is a late diastolic sound corresponding to late ventricular filling during an active atrial contraction. These are mechanical responses that can often be detected using various sensors (e.g. microphone, hydrophone, accelerometer, etc.).

Because the heart sounds are a result of cardiac muscle contracting or relaxing in response to an electrical cardiac signal, it will be appreciated that there is typically a delay between the electrical cardiac signal, indicated by the ECG 300, and the corresponding mechanical indication, indicated in the example shown by the heart sounds trace 302. For example, the P-wave of the ECG 300 is the electrical cardiac signal that triggers an atrial contraction of the heart. The S4 heart sound is the mechanical signal caused by the atrial contraction. In some cases, it may be possible to use this relationship between the P-wave and the S4 heart sound. For example, if one of these signals can be detected, their expected timing relationship can be used as a mechanism to search for the other. For example, if the P-wave can be detected, a window following the P-wave can be defined and searched in order to help find and/or isolate the corresponding S4 heart sound. In some cases, detection of both signals may be an indication of an increased confidence level in a detected atrial contraction. In some cases, detection of either signal may be sufficient to identify an atrial contraction. The identification of an atrial contraction may be used to identify an atrial contraction timing fiducial (e.g., a timing marker of the atrial contraction).

With traditional systems having transvenous leads, the intracardiac electrodes are placed to detect the atrial depolarization while also delivering pacing therapy to one or both ventricles. As a result, the circuitry of a single device would receive, directly, information for the P-wave allowing delivery at a timed interval of a pacing pulse to properly coordinate the ventricular pace with the atrial contraction and improve pumping efficiency. However, in order to provide a system including two or more LCPs capable of pacing both the right atrium and the right ventricle, the devices may be required to detect activity in a chamber different from that in which it is implanted. For example, with an LCP implanted within a ventricle, it may be difficult to detect the relatively small P-wave from within the ventricle, and as such, it is contemplated that the LCP may be configured to detect atrial activity without relying on the P-wave (e.g. using S4). The detected atrial activity may be used to identify an atrial timing fiducial that can be used as a basis for timing a pacing pulse in the ventricle (e.g. after an AV delay). Some illustrative but non-limiting devices and methods for detecting and utilizing atrial activity from the ventricle are described in commonly assigned Patent Application No. 62/593,642 entitled METHODS AND SYSTEMS FOR DETECTING ATRIAL CONTRACTION TIMING FIDUCIALS DURING VENTRICULAR FILLING FROM A VENTRICULARLY IMPLANTED LEADLESS CARDIAC PACEMAKER and filed on Dec. 1, 2017, Patent Application No. 62/593,703 entitled METHODS AND SYSTEMS FOR DETECTING ATRIAL CONTRACTION TIMING FIDUCIALS WITHIN A SEARCH WINDOW FROM A VENTRICULAR IMPLANTED LEADLESS CARDIAC PACEMAKER and filed on Dec. 1, 2017, Patent Application No. 62/593,688 entitled METHODS AND SYSTEMS FOR DETECTING ATRIAL CONTRACTION TIMING FIDUCIALS AND DETERMINING A CARDIAC INTERVAL FROM A VENTRICULARLY IMPLANTED LEADLESS CARDIAC PACEMAKER and filed on Dec. 1, 2017, Patent Application No. 62/593,662 entitled LEADLESS CARDIAC PACEMAKER WITH REVERSIONARY BEHAVIOR and filed on Dec. 1, 2017, which are hereby incorporated by reference.

In some examples, a time window for atrial artifact detection is defined during which the LCP 100 may specifically look for atrial artifacts (such as, but not limited to, atrial contraction) to determine an atrial timing fiducial. Such windows may be defined by analysis of the cardiac signals obtained from a patient using, for example, a detected ventricular event such as the R-wave/QRS complex or the T-wave of a previous heart beat as the starting point for timing delays 304, 306, as shown in FIG. 4. Timing delays 304, 306 may be dynamic based on the overall heart beat rate of the patient using data gathered from a patient or using a formula or accepted relationship. Other windows may be determined based on detected atrial artifacts and/or determined atrial events, as described in more detail herein.

In some cases, the relationship of certain electrical signals and/or mechanical indications may be used to predict the timing of other electrical signals and/or mechanical indications within the same heartbeat. Alternatively, or in addition, the timing of certain electrical signals and/or mechanical indications corresponding to a particular heartbeat may be used to predict the timing of other electrical signals and/or mechanical indications within a subsequent heartbeat.

Figure 5:
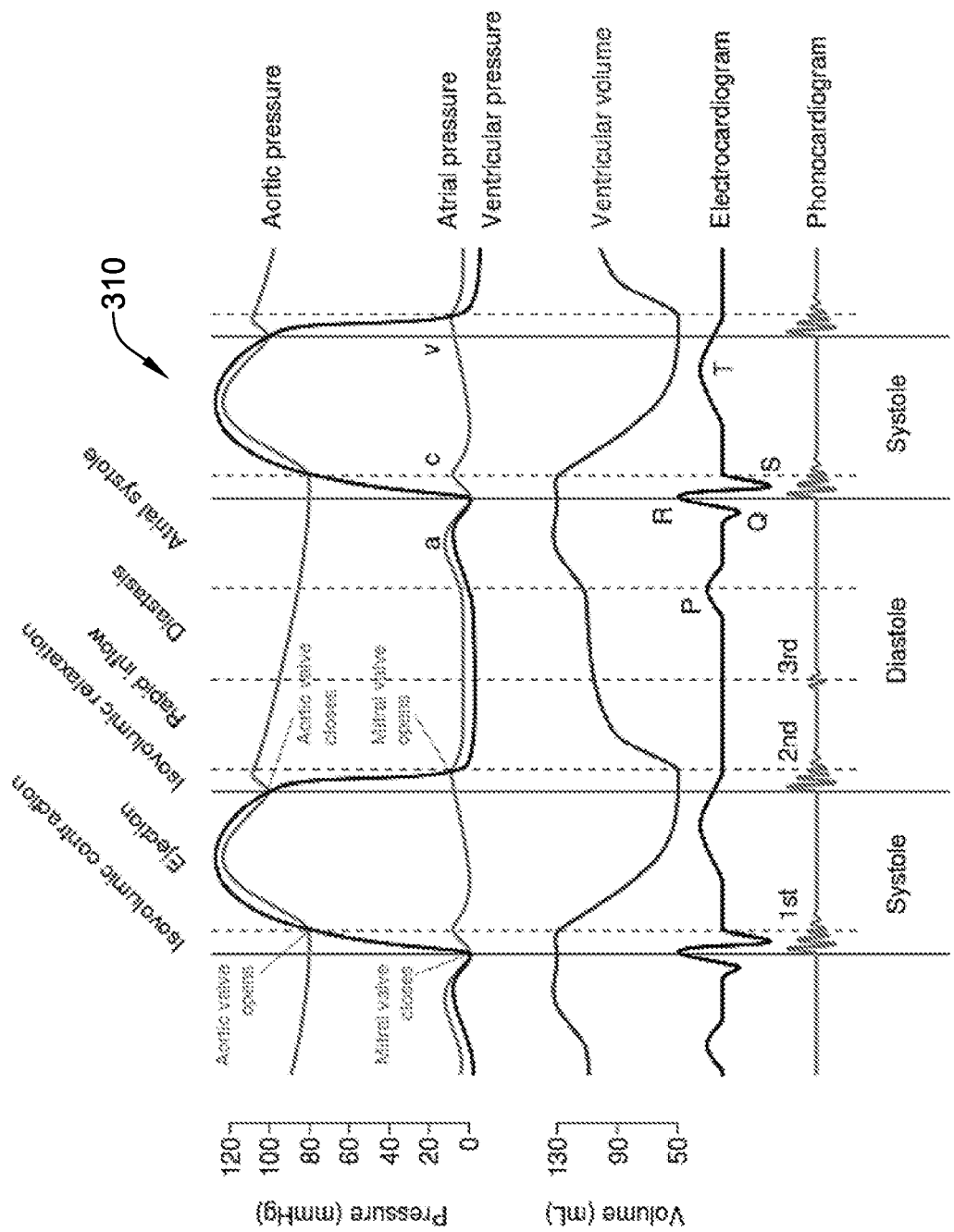
FIG. 5 is a graph showing example pressures and volumes within the heart over time.

It will be appreciated that as the heart undergoes a cardiac cycle, the blood pressures and blood volumes within the heart vary over time. FIG. 5 illustrates how these parameters correlate with the electrical signals and corresponding mechanical indications. FIG. 5 shows an illustrative example of the aortic pressure, left ventricular pressure, left atrial pressure, left ventricular volume, an electrocardiogram (ECG or egram), and heart sounds of the heart over two consecutive heart beats. A cardiac cycle may begin with diastole, and the mitral valve opens. The ventricular pressure falls below the atrial pressure, resulting in the ventricle filling with blood. During ventricular filling, the aortic pressure slowly decreases as shown. During systole, the ventricle contracts. When ventricular pressure exceeds the atrial pressure, the mitral valve closes, generating the S1 heart sound. Before the aortic valve opens, an isovolumetric contraction phase occurs where the ventricle pressure rapidly increases but the ventricle volume does not significantly change. Once the ventricular pressure equals the aortic pressure, the aortic valve opens and the ejection phase begins where blood is ejected from the left ventricle into the aorta. The ejection phase continues until the ventricular pressure falls below the aortic pressure, at which point the aortic valve closes, generating the S2 heart sound. At this point, the isovolumetric relaxation phase begins and ventricular pressure falls rapidly until it is exceeded by the atrial pressure, at which point the mitral valve opens and the cycle repeats.

Contractions of the atria are initiated near the end of ventricular diastole. The active atrial contraction pushes or forces additional volumes of blood into the ventricles (often referred to as "atrial kick") in addition to the volumes associated with passive filling. In some cases, the atrial kick contributes in the range of about 20% of the volume of blood toward ventricular preload. At normal heart rates, the atrial contractions are considered highly desirable for adequate ventricular filling. However, as heart rates increase, atrial filling becomes increasingly important for ventricular filling because the time interval between contractions for passive filling becomes progressively shorter. Cardiac pressure curves for the pulmonary artery, the right atrium, and the right ventricle, and the cardiac volume curve for the right ventricle, may be similar to those illustrated in FIG. 5. Typically, the cardiac pressure in the right ventricle is lower than the cardiac pressure in the left ventricle.

The heart sound signals shown in FIG. 5 can be recorded using acoustic sensors, for example a microphone, which may capture the acoustic waves resulted from such heart sounds. In another example, the heart sounds can be recorded using accelerometers or pressure sensors that capture the vibrations or pressure waves caused by the heart sounds. The heart sound signals can be recorded within or outside the heart. These are just examples.

In some cases, sensing atrial events or artifacts indicative of an atrial event may allow a device, such as LCP 100 implanted in the ventricle, to detect an atrial contraction, resulting in, for example, an atrial kick. In some cases, signals that provide an indication of an atrial contraction may include one or more of an S3 heart sound signal, an S4 heart sound signal, an A-wave signal (pressure wave) and a P-wave signal. In some cases, signals that can provide an indication of a ventricular contraction may include one or more of an R-wave, a ventricle pressure signal, a ventricle change in pressure signal (dP/dt), a ventricle wall acceleration signal, a ventricle twist signal, a blood flow rate signal, and a ventricle volume signal. These are just some examples.

Some other events or artifacts detected may include, but are not limited to, S1 heart sounds, S2 heart sounds, ventricular volume, ventricular wall dimension, cardiac tissue and/or blood vibration, atrium to ventricle blood movement or flow, ventricular wall and/or atrioventricular (AV) valve position, akinetic pressure, ventricular twist, and any other event or artifact suitable for identifying an atrial event, and/or combinations thereof.

Voltage may be used to detect P-waves, such as via an electrogram or an electrocardiogram (ECG). It is contemplated that, in some cases, an LCP implanted in the right ventricle may have a free end (e.g. end that is not affixed to the tissue) pointed towards the tricuspid valve. The electrodes of the LCP may be used to detect atrial depolarization (e.g., the p-wave). From the ventricle, the p-wave may be relatively small and difficult to detect. In some cases, the LCP may identify a time window around when the p-wave is expected, and the LCP may increase amplification and/or add special filtering and/or other signal processing to help identify the p-wave during the window. Alternatively, or in addition, the p-wave may be detected along with one or more other artifacts to help confirm an atrial contraction and to develop an atrial timing fiducial therefrom.

Pressure may be used to identify a number of different atrial artifacts. For example DC and/or near DC type pressure measurements (e.g. 0-10 Hz range) may be used to identify passive filling of the ventricle (e.g., akinetic pressure). Low frequency (e.g. 1-5 Hz range) AC type pressure measurements may be used to detect the A-wave (atrial pressure wave in the ventricle), while higher frequency (e.g. 15-30 Hz range) AC type pressure measurements may be used to detect heart sounds. These are just examples. Other suitable methods for measuring or detecting pressure in one or more heart chambers may also be used, as desired. Some illustrative but non-limiting pressure sensors and configurations for sensing pressure using an LCP are described in commonly assigned Patent Application No. 62/413,766 entitled "IMPLANTABLE MEDICAL DEVICE WITH PRESSURE SENSOR and filed on Oct. 27, 2016, and Patent Application No. 62/547,458, entitled IMPLANTABLE MEDICAL DEVICE WITH PRESSURE SENSOR and filed on Aug. 18, 2017, which are hereby incorporated by reference.

Impedance measurements may be used to determine ventricular volume changes which may then be used to infer a pressure wave (e.g. A-wave) due to an atrial contraction. In one example, as the volume of blood in the ventricle changes, the impedance between the electrodes of the LCP changes. It is contemplated that the rate of change in the volume (e.g., an increase in the rate of blood entering the ventricle and hence a faster change in volume of the ventricle) may be used to identify the start of active filling and thus an atrial contraction. Some illustrative uses of impedance measurements in the heart are described in commonly assigned patent application Ser. No. 15/630,677 entitled LEADLESS CARDIAC PACEMAKER FOR GENERATING CARDIAC PRESSURE-VOLUME LOOP and filed on Jun. 22, 2017, which is hereby incorporated by reference.

As blood enters the ventricle as a result of an atrial contraction, the ventricle may stretch. The stretching of the ventricle may be measured with a strain sensor. A strain sensor may require two or more points of fixation. Acceleration may be used to measure contractility of the heart H, as well as sounds. In some cases, cardiac output can be determined when acceleration measurements are combined with ventricle pressure, cardiac volume and/or other sensed parameters.

These are just examples, and it is contemplated that other artifacts, sensor modalities and/or combinations thereof may be used to identify an atrial event from the ventricle. In one additional example, a respiratory phase sensor may be used with other atrial artifacts described herein or by itself to help identify an atrial artifact.

In some instances, ultrasound may use a combined ultrasound source and sensor, although this is not required. The ultrasound source and sensor may be separately provided, as desired. It is contemplated that ultrasound imaging may be used in a device implanted in the ventricle to see the atrial wall (e.g., through the tricuspid valve), tricuspid closing, and/or a flow increase due to an atrial contraction to help identify an A-wave from the ventricle. In some cases, the ultrasound sensor may detect an atrial arrhythmia (e.g. atrial flutter or atrial fibrillation). During normal sinus rhythm (NSR), atrial blood flow into the ventricle typically includes two sequential components, an E (early) wave followed by an A (atrial) wave. During atrial arrhythmias, the E wave is often largely unchanged from that in NSR, however the A wave is either missing (atrial fibrillation) or smaller and much faster (atrial flutter). During a detected atrial arrhythmia, an LCP with an ultrasound sensor may modify its behavior (e.g. revert from VVD mode to VVI mode).

It should be noted that while the heart sounds are indicated as capable of being identified with an accelerometer, the accelerometer may actually measure or detect mechanical vibration associated with the heart sound, and not measure of detect the pressure of the sound waves themselves. In some cases, the measured artifact may not occur distinctly within one cardiac phase or another. For example, ventricular twist may be used to identify the end of active ventricular filling phase (e.g., ejection). Further, the S1 heart sound may occur at the end of active ventricular filling, while the S2 heart sound may occur shortly before the beginning of passive ventricular filling. These are just some examples.

In some cases, the LCP 100 may be configured to determine an atrial contraction timing fiducial based at least in part upon a sensed indication of an atrial contraction in a first heartbeat and/or a sensed indication of a ventricular contraction in the first heartbeat and/or one or more immediately preceding heartbeat(s). In some cases, the processing module 110 of the LCP 100 may be configured to generate and deliver a ventricle pacing pulse using the determined atrial contraction timing fiducial (e.g. after an A-V delay).

As described above, atrial events or artifacts indicative of an atrial event may be used by an LCP 10 implanted in the ventricle (e.g. right ventricle) to time a pacing pulse for the ventricle in support of, for example, treating bradycardia events. In some cases, the timing of the ventricle pacing pulse may be adjusted to improve the amount of blood entering the right ventricle through active filling from the atrium. In some instances, this may include adjusting an AV delay relative to an atrial timing fiducial (e.g., atrial kick). In some cases, a measured pressure change (or other atrial timing fiducial) over time may be used to support management of a CRT cardiac therapy (if placed in the left ventricle), patient health status monitoring and/or any other suitable goal. It is contemplated that detecting events in one of or both of the ventricle and atrium using a single LCP implanted in the ventricle may replicate a dual chamber system with only a single device. That is, a single device positioned in the ventricle may listen to both the ventricle and the atrium and pacing the ventricle accordingly (e.g., a VDD device).

Such a device may be paired with a second implantable device (e.g. LCP 50) positioned in the atrium. As the ventricular LCP 10 is capable of detecting and pacing according to detected atrial activity, the atrial LCP 50 does not necessarily need to communicate with the ventricular LCP 10 for the ventricular LCP 10 to appropriately time its pacing pulse. In some cases, an atrial LCP 50 may be configured to deliver a pacing pulse to the atrium based on atrial events and/or ventricular events. Some illustrative ventricular events may include but are not limited to a paced or intrinsic R-wave, ventricular pressure (e.g., dichotic notch) and/or a ventricle pacing pulse. In an example, an atrial LCP 50 may be an AAI or a ADD device. This is just one example. It is contemplated that the ventricular LCP 10 may use modes other than VDD and the atrial LCP 50 may use modes other than AAI. The pacing modes referenced herein (e.g. VDD, AAI, ADD, etc.) use the North American Society of Pacing and Electrophysiology (NASPE) and British Pacing and Electrophysiology Group (BPEG) pacemaker codes as outlined in Table 1 below:

TABLE 1

NASPE/BPEG Revised in 2002 NBG Pacemaker Code

| Position I (Chamber Paced) | Position II (Chamber Sensed) | Position III (Response to Sensed Event) | Position IV (Programmability, Rate Modulation) | Position V (Multisite Pacing) |
|---|---|---|---|---|
| O = none | O = none | O = none | | O = none |
| A = atrium | A = atrium | I = inhibited | | A = atrium |
| V = ventricle | V = ventricle | T = triggered | O = none | V = ventricle |
| D = dual (A + V) | D = dual (A + V) | D = dual (T + I) | R = rate modulation | D = dual (A + V) |

Miller RD. Miller's Anesthesia, 6$^{th}$ ed. Philadelphia: Elsevier, Inc. 2005, pp 1417.

An AAI device is a device pacing in the atrium, sensing in the atrium, and using inhibited pacing. It is contemplated that the ventricular LCP 10 and an atrial LCP 50 may not necessarily look for and/or use the same metric (e.g., atrial event and/or atrial timing fiducial) when determining when to pace. In other cases, the LCPs 10, 50 may look for the same metric or varying combinations of metrics, as desired. The control module of the ventricular LCP 10 may be configured to time the delivery of the pacing pulse in the ventricle based on the metric identifying the atrial event. It is contemplated that the ventricular LCP 10 may be programmed to synchronize the ventricular pacing therapy with the atrium in response to the detected atrial timing fiducials. In some cases, this may result in the ventricular LCP 10 delivering a pacing therapy in synchrony with a particular atrial event (e.g. after an AV delay). In other cases, this may result in the ventricular LCP 10 delivering a pacing pulse in response to a pacing pulse delivered by an atrial LCP 50. In other embodiments, the atrial LCP 50 may be programmed to synchronize the atrial pacing therapy with the ventricle in response to one or more detected ventricular timing fiducials. In some cases, this may result in an atrial LCP 50 delivering a pacing therapy in synchrony with a particular ventricular event. In other cases, this may result in the atrial LCP 50 delivering a pacing pulse in response to a pacing pulse delivered by the ventricular LCP 10.

In one example, the ventricular LCP 10 may look for (and pace based on) a change in sensed pressure, while the atrial LCP 50 may look for and pace based on sensed vibrations. The ventricular LCP 10 may be capable of detect pressure waves (e.g., a-waves) without any communication from the atrial LCP 50. In addition or alternatively to pacing based on sensed pressure waves, the ventricular LCP 10 may pace in response to a sensed pace pulse delivered by the atrial LCP 50. In another example, the ventricular LCP 10 may be configured to deliver a pace pulse in response to a direct wireless communication (e.g., conducted communication) from the atrial LCP 50.

While the ventricular LCP 10 has been described primarily as a VDD device, in some cases, the ventricular LCP 10 may be a VVI device. It is contemplated that a VVI ventricular LCP 10 may be paired with an ADD atrial LCP 50. In this example, the atrial LCP 50 may be configured to pace in response to a ventricular timing fiducial such as, but not limited to, a detected R-wave (without communication from the ventricular LCP 10). In addition to or in place of the detected R-wave, the atrial LCP 50 may be configured pace in response to a sensed right ventricular pacing pulse. In yet other instances, the atrial LCP 50 may be configured to pace in response to a direct communication (e.g., conducted communication) from the ventricular LCP 10. It is contemplated that the ventricular LCP 10 and/or atrial LCP 50 may be configured to switch between modes as necessary in response to changing cardiac conditions.

While it may be desirable to minimize wireless communication between the two devices 10, 50, some circumstances may require or necessitate communication. For example, the ventricular LCP 10 and an atrial LCP 50 may be configured to communicate for a period of time in response to a detected circumstance. In some cases, the period of time may be a specific length of time. In other cases, the period of time may correspond to a resolution of the circumstance(s) that initiated the need for communication between the devices.

In one example, if the ventricular LCP 10 temporarily fails to detect atrial activity because of noise, posture, patient activity or for any other reason, the atrial LCP 50 may be configured to communicate atrial events to the ventricular LCP 10 and the ventricular LCP 10 may synchronize the ventricular pacing therapy with the atrial beats based on those communications.

In some instances, the control module of the ventricular LCP 10 may be configured to determine a quality threshold for a timing window, which may reflect the quality of the atrial artifact signal identified during the timing window. For example, the control module may be configured to analyze or grade a current A-wave timing window. If the current A-wave timing window does not meet certain quality metrics (e.g., failure to detect an atrial cardiac event from the ventricle, an insufficient percent of cardiac cycles in which an A-Wave is detected, a low signal-to-noise ratio of the detected A-wave signal, etc.), the control module may discard the window and initiate communication with the atrial LCP 50. The ventricular LCP 10 may then receive an atrial timing fiducial from the atrial LCP 50, which is in a much better position to detect an atrial contraction, and may pace the ventricle based on the received atrial timing fiducial such that the pacing therapy delivered in the right ventricle RV is synchronized with the activity of the right atrium RA. In some cases, the atrial LCP 50 may be configured to communicate a pacing command to the ventricular LCP 10 rather than or in addition to sensed or detected atrial timing fiducials.

In some cases, the quality of the timing fiducial may be affected by a heart rate or a pacing rate. For example, a fast heart rate due to exercise or other factors may cause the signal to decrease in quality or blur. The control module of the ventricular LCP 10 and/or the atrial LCP 50 may be configured to initiate communication in response to a detected heart rate (e.g. in either chamber) above a predetermined threshold. In some cases, a timing fiducial may be considered to be of insufficient quality when, for example, a desired cardiac event was not detected, the SNR of the detected cardiac event is below a SNR threshold, a detected heart rate is above or below a corresponding heart rate threshold, and/or a detected pacing rate is above or below a corresponding heart rate threshold. These are just examples.

It is further contemplated that the control module of the ventricular LCP 10 and/or the atrial LCP 50 may be configured to initiate communication in response to a detected pacing rate (e.g. in either chamber) above a predetermined threshold. For example, in pacemaker mediated tachycardia, the ventricular LCP 10 and the atrial LCP 50 form an anterograde (atrium to ventricle [A→V]) limb of the cardiac circuit and the atrioventricular (AV) node may form a retrograde limb (ventricle to atrium [V→A]) of the cardiac circuit. The ventricular LCP 10 may pace the ventricle and the conduction system may propagate the signal in a retrograde manner to the atrium, generating an A-wave that triggers a subsequent ventricular pace. In the presence of elevated pacing rates above a predefined level, communication between the LCPs 10, 50 may be utilized to extend the post ventricular atrial refractory period for one or more heartbeats (e.g., extend the atrial refractory time for one or more cycles) and/or inhibit ventricular pacing for one or more heartbeats to help avoid or terminate such pacemaker mediated tachycardia.

For rate responsive pacing, communication between the ventricular LCP 10 and the atrial LCP 50 may be temporarily activated to increase (and/or decrease) a pacing rate. For example, when only one of the ventricular LCP 10 or the atrial LCP 50 are provided with an activity sensor (e.g., accelerometer), the device having the activity sensor may communicate to the other device a change in activity level of the patient that necessitates a change in pacing rate. It is contemplated that the device may communicate this information at any suitable time, such as every five seconds, every 10 seconds, every 20 seconds, etc., when the patient activity is elevated.

It is further contemplated that the ventricular LCP 10 and/or the atrial LCP 50 may be configured to communicate a desired mode change in response to a detected event or circumstance. For example, when atrial fibrillation is detected, the ventricular LCP 10 may switch to a VVI mode. It is contemplated that the atrial LCP 50 may communicate a command to the ventricular LCP 10 or the ventricular LCP 10 may automatically switch modes and communicate this change to the atrial LCP 50 such that the atrial LCP 50 may change or adjust its pacing algorithms accordingly. The atrial LCP 50 may be configured to detect the resolution of the atrial fibrillation. Upon the atrial LCP 50 detecting a resolution of atrial fibrillation, the atrial LCP 50 may communicate to the ventricular LCP 10 to switch back to VDD pacing therapy.

Figure 6:
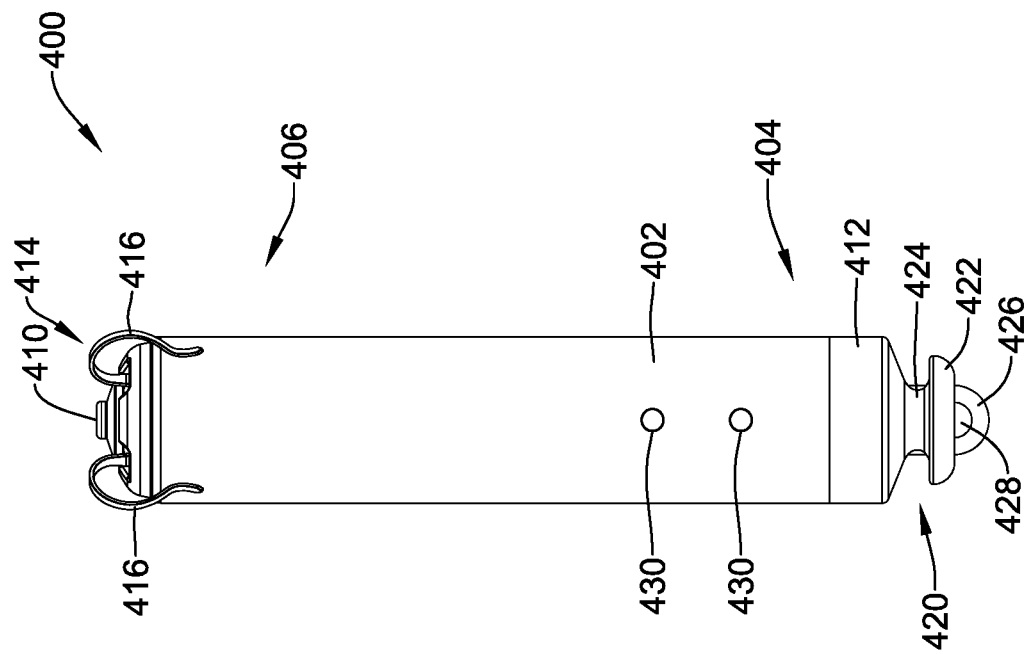
FIG. 6 is a side view of an illustrative LCP that may be used.

FIG. 6 is a side view of an illustrative implantable leadless cardiac pacemaker (LCP) 400 which may be positioned within the ventricle and/or atrium of the heart H, and may be configured to listen to both the ventricle and the atrium. The LCP 400 may be similar in form and function to the LCP 100 described above. The LCP 400 may include any of the sensing, electrical, control, and/or pacing modules and/or structural features described herein. The LCP 400 may include a shell or housing 402 having a proximal end 404 and a distal end 406. The illustrative LCP 400 includes a first electrode 410 secured relative to the housing 402 and positioned adjacent to the distal end 406 of the housing 402 and a second electrode 412 secured relative to the housing 402 and positioned adjacent to the proximal end 404 of the housing 402. In some cases, the housing 402 may include a conductive material and may be insulated along a portion of its length. A section along the proximal end 404 may be free of insulation so as to define the second electrode 412. The electrodes 410, 412 may be sensing and/or pacing electrodes to provide electro-therapy and/or sensing capabilities. The first electrode 410 may be capable of being positioned against or otherwise in contact with the cardiac tissue of the heart, while the second electrode 412 may be spaced away from the first electrode 410. The first and/or second electrodes 410, 412 may be exposed to the environment outside the housing 402 (e.g., to blood and/or tissue).

It is contemplated that the housing 402 may take a variety of different shapes. For example, in some cases, the housing 402 may have a generally cylindrical shape. In other cases, the housing 402 may have a half-dome shape. In yet other embodiments, the housing 402 may be a rectangular prism. It is contemplated that the housing may take any cross sectional shape desired, including but not limited to annular, polygonal, oblong, square, etc.

In some cases, the LCP 400 may include a pulse generator (e.g., electrical circuitry) and a power source (e.g., a battery) within the housing 402 to provide electrical signals to the electrodes 410, 412 to control the pacing/sensing electrodes 410, 412. While not explicitly shown, the LCP 400 may also include a communications module, an electrical sensing module, a mechanical sensing module, and/or a processing module, and the associated circuitry, similar in form and function to the modules 102, 106, 108, 110 described above. The various modules and electrical circuitry may be disposed within the housing 402. Electrical communication between the pulse generator and the electrodes 410, 412 may provide electrical stimulation to heart tissue and/or sense a physiological condition.

In the example shown, the LCP 400 includes a fixation mechanism 414 proximate the distal end 406 of the housing 402. The fixation mechanism 414 is configured to attach the LCP 400 to a wall of the heart H, or otherwise anchor the LCP 400 to the anatomy of the patient. As shown in FIG. 6, in some instances, the fixation mechanism 414 may include one or more, or a plurality of hooks or tines 416 anchored into the cardiac tissue of the heart H to attach the LCP 400 to a tissue wall. In other instances, the fixation mechanism 414 may include one or more, or a plurality of passive tines, configured to entangle with trabeculae within the chamber of the heart H and/or a helical fixation anchor configured to be screwed into a tissue wall to anchor the LCP 400 to the heart H. These are just examples.

The LCP 400 may further include a docking member 420 proximate the proximal end 404 of the housing 402. The docking member 420 may be configured to facilitate delivery and/or retrieval of the LCP 400. For example, the docking member 420 may extend from the proximal end 404 of the housing 402 along a longitudinal axis of the housing 402. The docking member 420 may include a head portion 422 and a neck portion 424 extending between the housing 402 and the head portion 422. The head portion 422 may be an enlarged portion relative to the neck portion 424. For example, the head portion 422 may have a radial dimension from the longitudinal axis of the LCP 400 that is greater than a radial dimension of the neck portion 424 from the longitudinal axis of the LCP 400. In some cases, the docking member 420 may further include a tether retention structure 426 extending from or recessed within the head portion 422. The tether retention structure may define an opening 428 configured to receive a tether or other anchoring mechanism therethrough. The retention structure may take any shape that provides an enclosed perimeter surrounding the opening such that a tether may be securely and releasably passed (e.g., looped) through the opening 428. In some cases, the retention structure may extend though the head portion 422, along the neck portion 424, and to or into the proximal end 404 of the housing 402. The docking member 420 may be configured to facilitate delivery of the LCP 400 to the intracardiac site and/or retrieval of the LCP 400 from the intracardiac site. While this describes one example docking member 420, it is contemplated that the docking member 420, when provided, can have any suitable configuration.

It is contemplated that the LCP 400 may include one or more sensors 430 coupled to or formed within the housing 402 such that the sensor(s) is exposed to and/or otherwise operationally coupled with (e.g., responsive to) the environment outside the housing 402 to measure or detect various artifacts within the heart. The one or more sensors 430 may be of a same modality or a combination of two or more different sensing modalities, as desired. For example, the one or more sensors 430 may be use voltage, pressure, sound, ultrasound, impedance, strain, acceleration, flow, and/or rotation to detect P-waves, A-waves, R-waves, E-waves, S1-S4 heart sounds, ventricular volume, ventricular wall dimensions, cardiac tissue and/or blood vibration, atrium to ventricle blood movement, ventricular wall and/or atrioventricular valve position, akinetic pressure, and/or ventricular twist. The sensors may be a part of, coupled to, and/or in electrical communication with a sensing module disposed within the housing 402. In addition to sensing artifacts within the heart, the sensing module may be further configured to detect physiological conditions that may impact the LCP's ability to detect artifacts including, but not limited to posture, activity and/or respiration. The use of two or more sensors in combination may allow for the removal of some common mode noise (e.g., may eliminate gross body motion).

In some cases, the one or more sensors 430 may be coupled to an exterior surface of the housing 402. In other cases, the one or more sensors 430 may be positioned within the housing 402 with an artifact acting on the housing and/or a port on the housing 402 to affect the sensor 430. In one illustrative example, if the LCP 400 is placed in the right ventricle, the sensor(s) 430 may be a pressure sensor configured to measure a pressure within the right ventricle. If the LCP 400 is placed in another portion of the heart (such as one of the atriums or the left ventricle), the pressures sensor(s) may measure the pressure within that portion of the heart. In some cases, the sensor(s) 430 may be sensitive enough to detect an artifact in a heart chamber different from the chamber in which the LCP 400 is positioned. For example, in some instances a sensor 430 may detect a pressure change caused by an atrial contraction (e.g., atrial kick) when the LCP 400 is placed in the right ventricle.

It is contemplated that a ventricular LCP 10 and an atrial LCP 50 may be structurally similar (although not required) but may differ in the programming of the control module. For example, as the implant location varies, the control modules of the ventricular LCP 10 and the atrial LCP 50 may need to account for the delay in pacing pulse. In one example, the interval from the atrial fiducial to the ventricular pace will be different for different types of atrial fiducials The AV delay for a P-wave to ventricular pacing may be longer than the AV delay for an A-wave to ventricular pacing. Further AV delays after an atrial pace may be different (e.g., longer) than after an intrinsic atrial event. As can been seen, the respective devices will need to account for the fiducial (e.g., atrial and/or ventricular) used to time the pacing pulse.

While it is desirable to identify an atrial contraction often associated with the A-wave, the A-wave can be difficult to detect as it may be very small in magnitude and detection of it may come and go. It is contemplated that a combination of sensor modalities and/or measured atrial artifacts may be used to help identify an atrial timing fiducial. For example, it is contemplated that any of the sensor modalities identified herein may be combined with any other sensor modality to identify an atrial timing fiducial and/or ventricular timing fiducial. In some cases, a pressure signal may be used to determine a number of parameters. For example, a pressure signal may be used to determine or detect an A-wave (atrial kick). In another example, the pressure signal may be used to determine or detect a pressure pulse or pressure vibrations associated with S4, which may, for example, be in the 15-30 Hz range. In some cases, the S4 heart sound may be easier to detect using a pressure signal from a pressure sensor than from an accelerometer signal from accelerometer or using an acoustic signal from an acoustic sensor, particularly since the ventricular pressure is not changing substantially during this time period (ventricle is filling) and since there may be a great deal of unwanted signal (i.e. noise) in the accelerometer signal due to patient activity. In another example, a pressure signal may be used to determine a change in ventricle pressure relative to time (dP/dt).

In some cases, the circuitry and/or processing module of the LCP 400 may also be configured determine an atrial contraction and/or ventricular timing fiducial based at least in part upon two or more of a signal received from the electrical sensing module, mechanical sensing module, and/ or communication module. In some cases, the electrical cardiac signal received via the electrode arrangement 410, 412 may include at least a portion of an electrocardiogram (ECG). In some cases, the electrical cardiac signal received via electrode arrangement 410, 412 may include a P-wave. In some instances, the electrical cardiac signal received via the electrode arrangement 410, 412 may include a QRS complex, from which a QRS width can be determined. In some cases, the electrical cardiac signal received via electrode arrangement 410, 412 may include two consecutive R waves, from which an R-wave to R-wave interval can be determined. In some cases, the electrical cardiac signal may include a conducted or other communicated electrical signal from another device (e.g. SICD device, atrial LCP, etc.) that includes an indication of an atrial or other contraction of the heart H. In some cases, the processing module and/or circuity may be configured to generate and deliver a ventricle pacing pulse using the atrial contraction timing fiducial. Uses of the sensors, determination of timing windows, determination of pacing delivery, and reversionary behavior of ventricularly implanted LCPs pacing based on atrial events are described in commonly assigned Patent Application No. 62/593,642 entitled METHODS AND SYSTEMS FOR DETECTING ATRIAL CONTRACTION TIMING FIDUCIALS DURING VENTRICULAR FILLING FROM A VENTRICULARLY IMPLANTED LEADLESS CARDIAC PACEMAKER and filed on Dec. 1, 2017, Patent Application No. 62/593,703 entitled METHODS AND SYSTEMS FOR DETECTING ATRIAL CONTRACTION TIMING FIDUCIALS WITHIN A SEARCH WINDOW FROM A VENTRICULAR IMPLANTED LEADLESS CARDIAC PACEMAKER and filed on Dec. 1, 2017, Patent Application No. 62/593,688 entitled METHODS AND SYSTEMS FOR DETECTING ATRIAL CONTRACTION TIMING FIDUCIALS AND DETERMINING A CARDIAC INTERVAL FROM A VENTRICULARLY IMPLANTED LEADLESS CARDIAC PACEMAKER and filed on Dec. 1, 2017, Patent Application No. 62/593,662 entitled LEADLESS CARDIAC PACEMAKER WITH REVERSIONARY BEHAVIOR and filed on Dec. 1, 2017, all of which are hereby incorporated by reference.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed is:

1. A leadless cardiac pacemaker (LCP) system configured to sense cardiac activity and to deliver pacing therapy to a patient's heart, the LCP system comprising:
    a first LCP configured to be positioned in a first chamber of a heart and to deliver a first pacing therapy to the first chamber of the heart, the first LCP comprising:
        a housing;
        a first electrode secured relative to the housing and exposed to the environment outside of the housing;
        a second electrode secured relative to the housing and exposed to the environment outside of the housing;
        a sensing module configured to detect a cardiac event of a second chamber of the heart and generate a corresponding first timing fiducial; and
        a control module operatively coupled to the first electrode, the second electrode, and the sensing module of the first LCP;
    a second LCP configured to be positioned in the second chamber of the heart and to deliver a second pacing therapy to the second chamber of the heart, the second LCP comprising:
        a housing;
        a first electrode secured relative to the housing and exposed to the environment outside of the housing;
        a second electrode secured relative to the housing and exposed to the environment outside of the housing;
        a sensing module configured to detect a cardiac event of the first chamber and/or the second chamber of the heart; and
        a control module operatively coupled to the first electrode, the second electrode, and the sensing module of the second LCP;
    wherein the control module of the first LCP is configured to time the delivery of at least part of the first pacing therapy of the first LCP based, at least in part, on the first timing fiducial.

2. The LCP system of claim 1, wherein the first pacing therapy delivered by the first LCP in the first chamber is synchronized with the second chamber of the heart based, at least in part, on the first timing fiducial.

3. The LCP system of claim 2, wherein the first LCP and the second LCP are configured to wirelessly communicate with each other, and wherein when the first timing fiducial is of insufficient quality the first pacing therapy delivered by the first LCP in the first chamber is synchronized with the second chamber of the heart via a communication between the second LCP and the first LCP.

4. The LCP system of claim 3, wherein the first timing fiducial is of insufficient quality when:
    the cardiac event was not detected;
    the signal to noise ratio (SNR) of the detected cardiac event is below a SNR threshold;
    a detected heart rate in the first and/or second chamber is above a heart rate threshold; or
    a detected pacing rate in the first and/or second chamber is above a pacing rate threshold.

5. The LCP system of claim 3, wherein the first LCP and the second LCP are configured to wirelessly communicate with each other using conducted communication.

6. The LCP system of claim 1, wherein the first chamber is the right ventricle of the heart and the second chamber is the right atrium of the heart.

7. The LCP system of claim 6, wherein the sensing module of the first LCP comprises an electrical signal sensor and a pressure sensor.

8. The LCP system of claim 6, wherein the sensing module of the first LCP comprises an electrical signal sensor and an accelerometer.

9. The LCP system of claim 6, wherein the cardiac event of the second chamber comprises one or more of an atrial pressure wave, an atrial electrical P-signal, and an atrial pace pulse.

10. The LCP system of claim 6, wherein the first pacing therapy comprises a VVI or VDD pacing therapy, and the second pacing therapy comprises an AAI or ADD pacing therapy.

11. The LCP system of claim 10, wherein the second LCP is configured to detect atrial fibrillation, and when the second LCP detects atrial fibrillation the second LCP is configured to wirelessly communicate with the first LCP to switch the first LCP to a VVI pacing therapy.

12. The LCP system of claim 11, wherein the second LCP is configured to detect when an atrial fibrillation resolves, and when the second LCP detects that an atrial fibrillation resolves, the second LCP is configured to wirelessly communicate with the first LCP to switch the first LCP to a VDD pacing therapy.

13. The LCP system of claim 1, wherein the first chamber is the right atrium of the heart and the second chamber is the right ventricle of the heart.

14. The LCP system of claim 13, wherein the cardiac event comprises one or more of a ventricle electrical R-signal and a ventricle pace pulse.

15. The LCP system of claim 13, wherein the first pacing therapy comprises an AAI or ADD pacing therapy, and the second pacing therapy comprises a VVI or VDD pacing therapy.

16. A leadless cardiac pacemaker (LCP) system configured to sense cardiac activity and to deliver pacing therapy to a patient's heart, the LCP system comprising:

- a first LCP configured to be positioned in an atrium of a heart;
- a second LCP configured to be positioned in a ventricle of the heart;
- the first LCP configured to detect a cardiac event of the ventricle of the heart and generate a corresponding ventricular timing fiducial; and
- the first LCP is configured to deliver a pacing therapy to the atrium of the heart, wherein the pacing therapy delivered by the first LCP in the atrium is synchronized with the ventricle of the heart using the ventricular timing fiducial.

17. The LCP system of claim 16, wherein the first LCP and the second LCP are configured to wirelessly communicate with each other by conducted communication, and wherein when the ventricular timing fiducial is of insufficient quality the pacing therapy delivered by the first LCP in the atrium is synchronized with the ventricle of the heart via a communication between the second LCP and the first LCP.

* * * * *